(12) United States Patent
Cuccia et al.

(10) Patent No.: US 11,751,769 B2
(45) Date of Patent: Sep. 12, 2023

(54) SYSTEMS AND METHODS FOR ASSESSING DIABETIC CIRCULATORY COMPLICATIONS

(71) Applicant: MODULATED IMAGING, INC., Irvine, CA (US)

(72) Inventors: David Cuccia, Costa Mesa, CA (US); Amaan Mazhar, Corona Del Mar, CA (US)

(73) Assignee: MODULATED IMAGING, INC., Irvine, CA (US)

( * ) Notice: Subject to any disclaimer, the term of this patent is extended or adjusted under 35 U.S.C. 154(b) by 762 days.

(21) Appl. No.: 16/565,045

(22) Filed: Sep. 9, 2019

(65) Prior Publication Data

US 2020/0107732 A1   Apr. 9, 2020

Related U.S. Application Data

(63) Continuation of application No. PCT/US2018/023856, filed on Mar. 22, 2018.
(Continued)

(51) Int. Cl.
*A61B 5/02* (2006.01)
*A61B 5/00* (2006.01)
(Continued)

(52) U.S. Cl.
CPC ........ *A61B 5/02007* (2013.01); *A61B 5/0064* (2013.01); *A61B 5/0077* (2013.01);
(Continued)

(58) Field of Classification Search
CPC . A61B 5/02007; A61B 5/0064; A61B 5/0077; A61B 5/14546; A61B 5/14551;
(Continued)

(56) References Cited

U.S. PATENT DOCUMENTS 6,990,364 B2   1/2006 Ruchti et al.
8,548,570 B2   10/2013 Freeman et al.
(Continued)

FOREIGN PATENT DOCUMENTS

WO   WO 2014/074720 A1   5/2014

OTHER PUBLICATIONS

EP, 18771715.2 Extended Search Report, dated Nov. 9, 2020.
(Continued)

*Primary Examiner* — Eric F Winakur
*Assistant Examiner* — Abid A Mustansir
(74) *Attorney, Agent, or Firm* — ONE LLP

(57) ABSTRACT

Systems and methods directed to the assessment of circulatory complications due to advancement of diabetes. Embodiments include an optical measurement device having a light source with one or more wavelengths and configured to illuminate an area of tissue, a detector configured to capture the light reflecting from one or more layers of the tissue at the one or more illumination wavelengths, a processor configured to compute, based on the detected signal of layer extracted circulatory data, one or more estimates of tissue vascular health, and a display or communication device (e.g., electronic data transfer) configured to store or report the tissue vascular health. In exemplary embodiments, the distribution of chromophores such as hemoglobin in different layers of skin is extracted using a combination of structured light in the visible and near-infrared regime.

12 Claims, 34 Drawing Sheets

Related U.S. Application Data

(60) Provisional application No. 62/475,059, filed on Mar. 22, 2017.

(51) Int. Cl.
  *A61B 5/145* (2006.01)
  *A61B 5/1455* (2006.01)

(52) U.S. Cl.
  CPC ...... *A61B 5/14546* (2013.01); *A61B 5/14551* (2013.01); *A61B 5/486* (2013.01); *A61B 5/7275* (2013.01); *A61B 5/748* (2013.01); *A61B 5/7425* (2013.01); *A61B 2562/223* (2013.01)

(58) Field of Classification Search
  CPC ..... A61B 5/486; A61B 5/7275; A61B 5/7425; A61B 5/748; A61B 2562/223; A61B 5/0073; A61B 5/02042; A61B 5/441; A61B 5/445; A61B 5/443; A61B 5/447; A61B 5/0075; A61B 5/0002; A61B 5/4842
  See application file for complete search history.

(56) References Cited

U.S. PATENT DOCUMENTS

| | | | |
|---|---|---|---|
| 8,868,157 | B1 | 10/2014 | Soliz |
| 8,892,192 | B2 | 11/2014 | Cuccia et al. |
| 9,220,412 | B2 | 12/2015 | Cuccia |
| 11,166,652 | B2 | 11/2021 | Cuccia et al. |
| 2003/0139667 | A1 | 7/2003 | Hewko et al. |
| 2005/0273011 | A1* | 12/2005 | Hattery ................ A61B 5/0075 600/476 |
| 2007/0016079 | A1 | 1/2007 | Freeman et al. |
| 2007/0024946 | A1 | 2/2007 | Panasyuk et al. |
| 2007/0038042 | A1 | 2/2007 | Freeman et al. |
| 2010/0210931 | A1* | 8/2010 | Cuccia ................ A61B 5/445 600/328 |
| 2010/0312076 | A1* | 12/2010 | Bly ........ A61B 5/412 600/301 |
| 2011/0124987 | A1 | 5/2011 | Papazoglou et al. |
| 2014/0018649 | A1 | 1/2014 | Jespersen et al. |
| 2014/0213910 | A1 | 7/2014 | Durkin et al. |
| 2014/0257113 | A1 | 9/2014 | Panasyuk et al. |
| 2014/0268163 | A1 | 9/2014 | Milner et al. |
| 2014/0276014 | A1* | 9/2014 | Khanicheh ........... A61B 5/0073 600/425 |
| 2015/0265150 | A1 | 9/2015 | Darty et al. |
| 2015/0265195 | A1 | 9/2015 | Darty et al. |
| 2015/0327777 | A1 | 11/2015 | Kostic et al. |
| 2016/0069743 | A1 | 3/2016 | McQuilkin et al. |

OTHER PUBLICATIONS

JP, 2019-551600 Office Action, dated Mar. 11, 2022.
WO, PCT/US2018/023856 ISR and Written Opinion, dated Jul. 5, 2018.
Boezeman, R., et al., "In vivo measurements of regional hemoglobin oxygen saturation values and limb-to-arm ratios of near-infrared spectroscopy for tissue oxygenation monitoring of lower extremities in healthy subjects", Medical Devices: Evidence and Research, 2015, vol. 8, pp. 31-36.
Tseng, S.H., et al., "Chromosphere concentrations, absorption and scattering properties of human skin in-vivo", Optics Express, 2009, vol. 17, No. 17, pp. 14599-14617.
TW, 107109908 Office Action, dated Dec. 22, 2021.
CN, 201880019801.9 First Office Action, dated Dec. 15, 2021.

\* cited by examiner

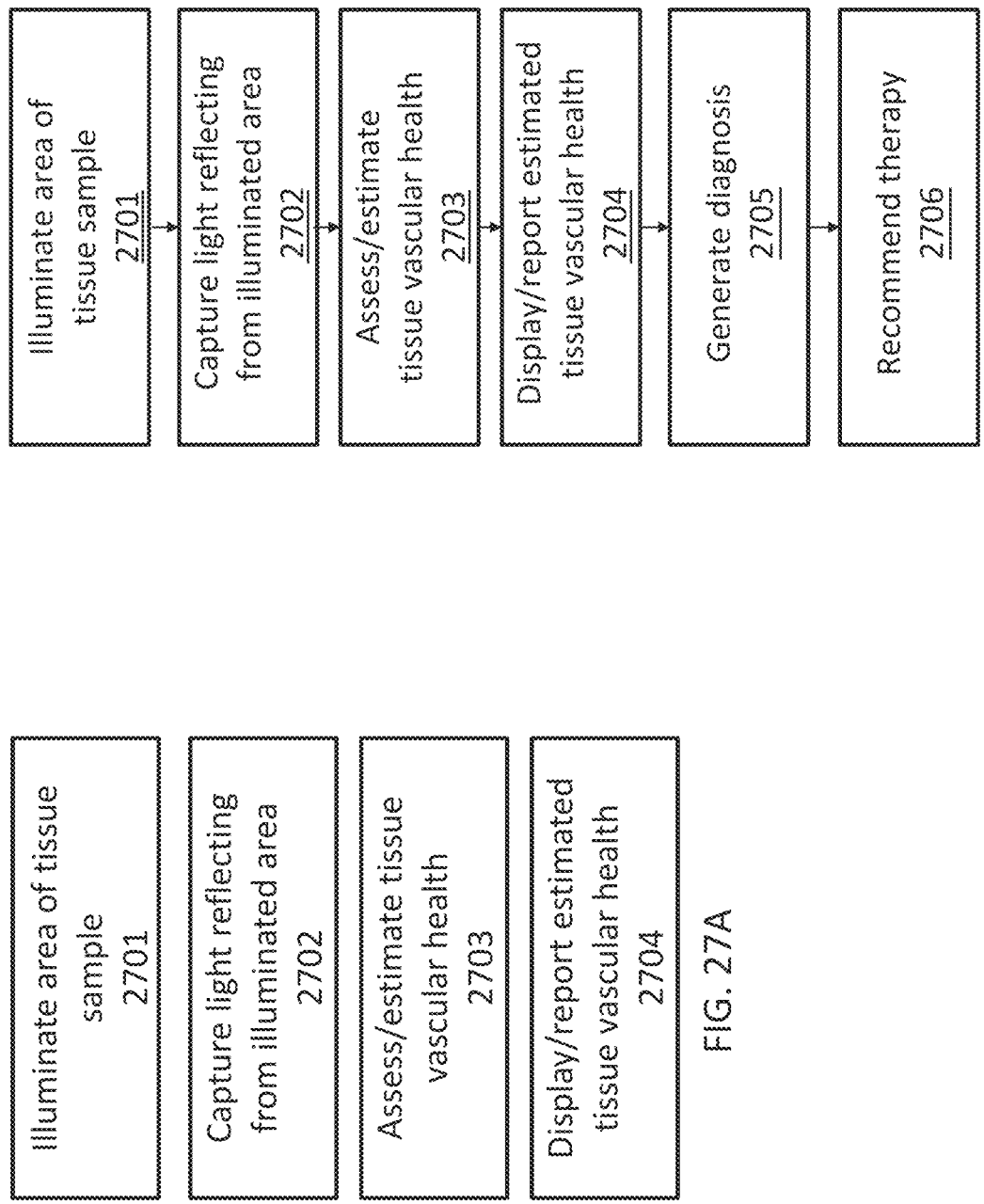

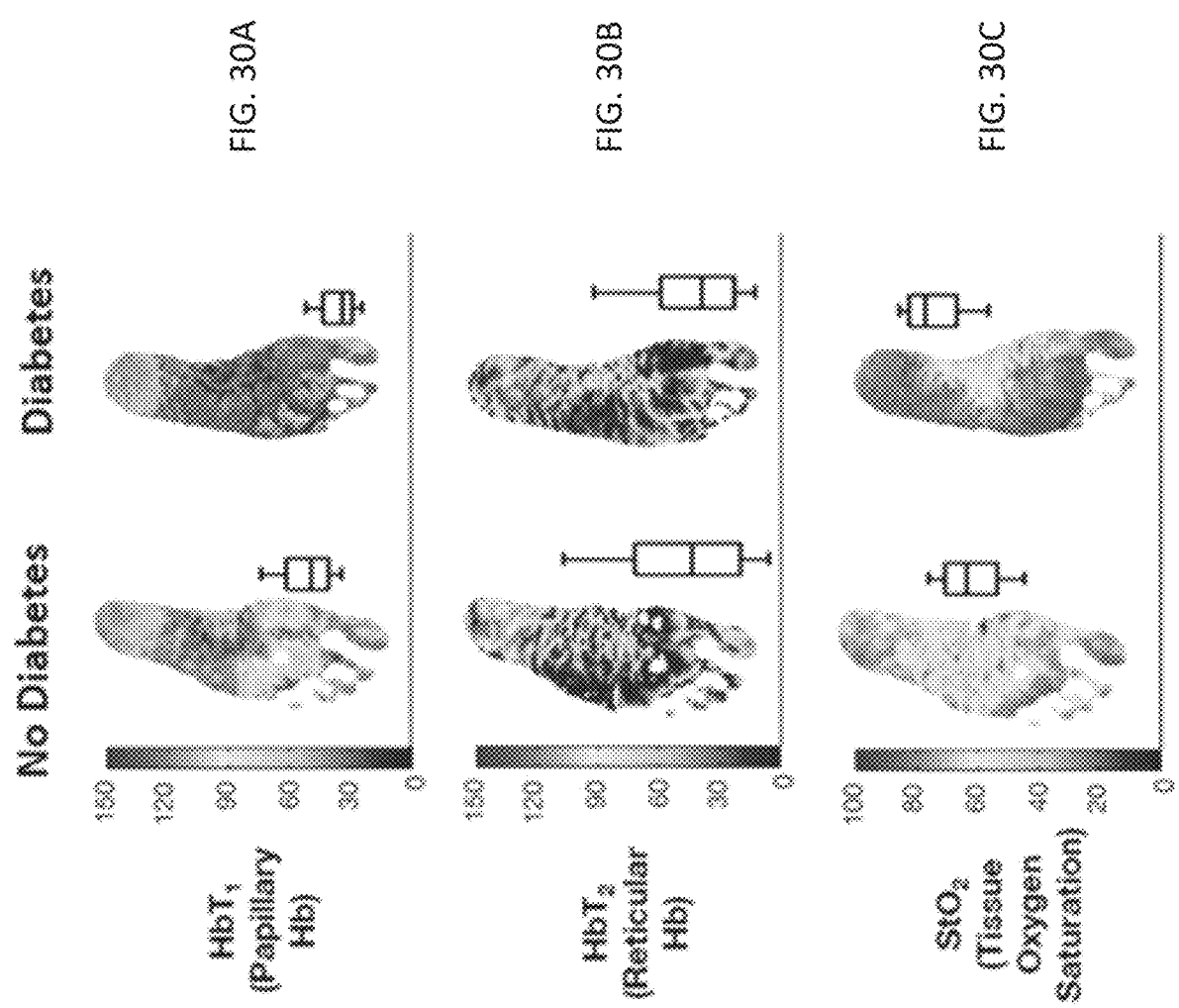

SYSTEMS AND METHODS FOR ASSESSING DIABETIC CIRCULATORY COMPLICATIONS

CROSS REFERENCE TO RELATED APPLICATIONS

The present application is a continuation of International Patent Appl. No. PCT/US18/23856, filed Mar. 22, 2018, which claims the benefit of priority to U.S. Provisional Application No. 62/475,059, filed Mar. 22, 2017, the disclosures of each of which are incorporated herein by reference in their entireties for all purposes.

FIELD

The embodiments described herein relate generally to optical measurement of tissue media, and, more particularly, to systems and methods directed to the assessment of circulatory complications due to advancement of diabetes.

BACKGROUND

Type two diabetes is one of the fastest growing epidemics globally. In the United States alone, the type two diabetic population is approximated at 29 M and world-wide this population is estimated to grow to 592 million by 2035. One of the major implications in diabetes is impaired circulation due to onset of autonomic microvascular disease. As a result, patients are particularly susceptible to chronic wounds due to compromised circulation. In fact, 25% of patients with diabetes are expected to form an ulcer on their foot in their lifetime.

The reasons for onset of diabetic foot ulcers is multifaceted. The most common event that causes ulcers to form is poor offloading (due to poor fitting shoes). A physical traumatic event such as stepping on a sharp object can also create an open wound. Once the wound is created it is difficult to heal due to poor peripheral circulation.

One of the challenges in the prevention of diabetic foot ulcers is stratifying patients at risk for ulceration. The most at-risk patients require advanced foot care by specialists (podiatrists, vascular surgeons) who may prescribe custom shoes, orthotics, drugs, and/or preventive surgery. There are clinical recommendations set forth by the medical community for stratifying patients at risk that are based on progression of diabetes severity. One study reported that patients with sensory neuropathy had 4.5% chance of developing an ulcer whereas patients with sensory neuropathy and diagnosed vascular disease are 3 times more likely at 13.8%. This rate is compared to patients with diabetes and no other known comorbidities getting ulcers at rate of 2%. Based on these occurrence rates, an at-risk patient's frequency of examinations with a foot care specialist is directly tied to these clinically assessed level of diabetic severity (i.e. presence of sensory neuropathy, presence of peripheral vascular disease ("PVD")).

One of the challenges in patients with diabetes is really understanding the extent of circulation issues and categorizing patients accurately within the recommended clinical groups. For example, loss of sensation in the foot occurs due to progressive neuropathic damage as circulation is compromised over an extended period time. Additionally, the lack of reliability in the current testing methods (i.e. ankle brachial index (ABI), or toe brachial index, TBI) make it difficult to accurately assess peripheral vascular disease in patients with diabetes.

Therefore, it is desirable to provide improved systems and methods that facilitate the assessment of circulatory complications due to advancement of diabetes.

SUMMARY

The various embodiments provided herein are directed to systems and methods that facilitate the assessment of circulatory complications due to advancement of diabetes. In exemplary embodiments provided herein, an optical measurement device includes a light source with one or more wavelengths, the light source is configured to illuminate an area of tissue; a detector configured to capture the light reflecting from one or more layers of the tissue at the one or more illumination wavelengths; a processor configured to compute, based on the detected signal of layer extracted circulatory data, one or more estimates of tissue vascular health, and a display or communication device (e.g., electronic data transfer) configured to store or report the tissue vascular health.

In exemplary embodiments provided herein, the distribution of hemoglobin ("Hb") in different layers of skin is extracted using a combination of structured light in the visible and near-infrared regime. For example, Hb can be measured in two layers of skin—a first layer, referred to as the superficial papillary dermis (capillary-weighted), and a second layer, referred to as the deeper reticular dermis (arteriole/venule weighted). The ability to measure circulation via layered measurements with a single snapshot and with added insight on compartment Hb distribution enables the acquisition of greater knowledge about circulation and, thus, tissue health—particularly in patients with diabetes. For example, superficial Hb (HbT1) is lower in patients with diabetes than patients with no diabetes and, in patients with diabetes, the superficial Hb (HbT1) is lower in patients with sensory neuropathy than patients without sensory neuropathy. This is likely due to arterio-venous shunting of blood flow that occurs when there is peripheral nerve-damage that damages autonomic regulation of blood flow.

The above change in circulation correlates with and/or precedes protective sensation loss. As a result, the detection of such changes in circulation can be used for early diagnosis of nerve degradation and a precursor to neuropathic ulceration.

Similarly, elevated StO2 levels (when sampling superficial and deep Hb) can be an indication of poor O2 extraction as a result of compromised transport and/or low consumption rather than excessive blood supply.

In patients with calluses, the superficial Hb in localized areas can be lower due to structural and/or functional changes in the skin. This can help identify regional compromised circulation in localized areas.

The compartment distribution can inform the status of peripheral vascular disease ("PVD"), particularly in patients with diabetes. For example, an increase in HbT2 and a decrease in HbT1 occurs in patients with vascular disease, which tends to be due to a loss of circulatory pressure.

Other systems, methods, features and advantages of the example embodiments will be or will become apparent to one with skill in the art upon examination of the following figures and detailed description.

BRIEF DESCRIPTION OF FIGURES

The details of the example embodiments, including structure and operation, may be gleaned in part by study of the accompanying figures, in which like reference numerals refer to like parts. The components in the figures are not necessarily to scale, emphasis instead being placed upon illustrating the principles of the invention. Moreover, all illustrations are intended to convey concepts, where relative sizes, shapes and other detailed attributes may be illustrated schematically rather than literally or precisely.

FIGS. 27A and 27B illustrate an exemplary method for estimating tissue vascular health according to embodiments of the present disclosure.

FIGS. 30A, 30B and 30C illustrate graphs comparing foot perfusion in diabetic and non-diabetic patients based on multi-layer extracted hemoglobin data; FIG. 30A compares intensity value maps and distributions of the intensity values of papillary Hb (HbT1) for diabetic and non-diabetic patients; FIG. 30B compares intensity value maps and distributions of the intensity values of reticular Hb (HbT2) for diabetic and non-diabetic patients; FIG. 30C compares intensity value maps and distributions of the intensity values of papillary tissue oxygen saturation (StO2) for diabetic and non-diabetic patients.

It should be noted that elements of similar structures or functions are generally represented by like reference numerals for illustrative purpose throughout the figures. It should also be noted that the figures are only intended to facilitate the description of the exemplary embodiments.

DETAILED DESCRIPTION

Figures 1A, 1B:
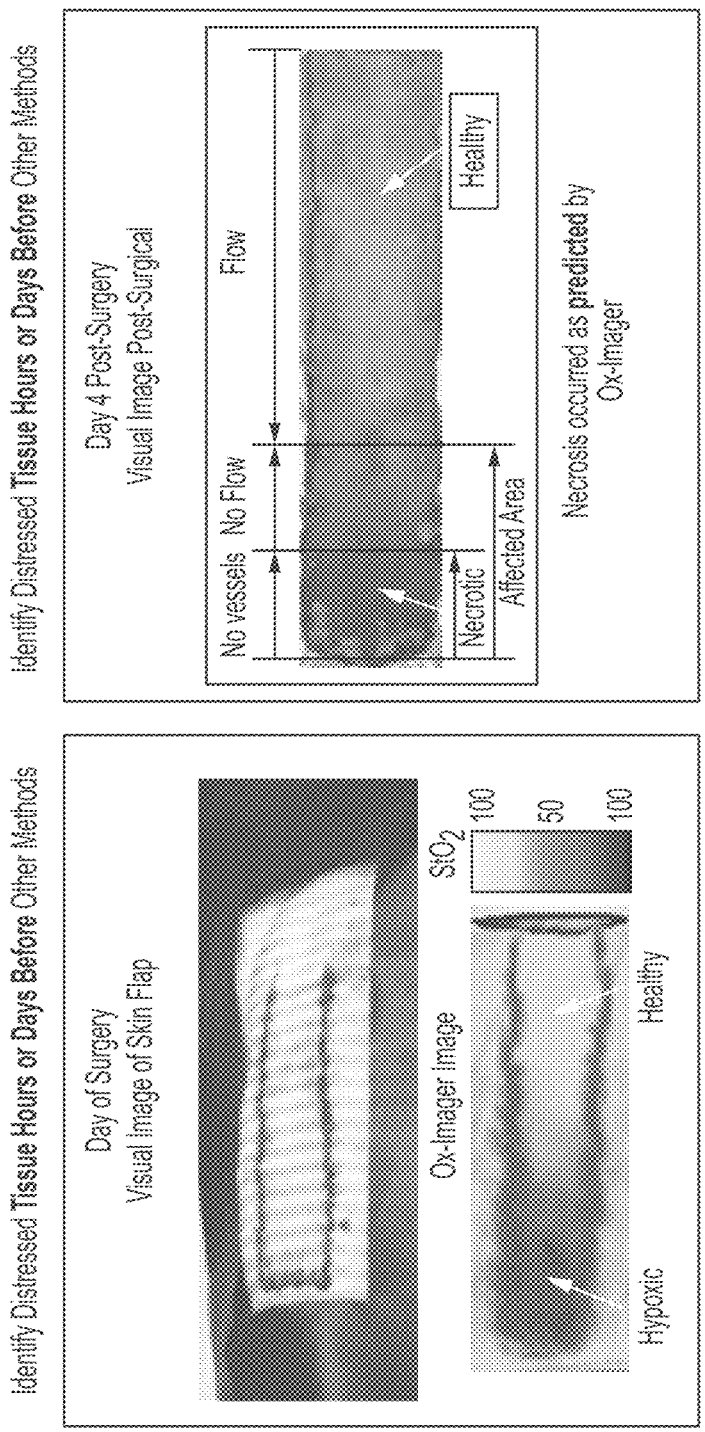
FIGS. 1A and 1B illustrate modulated imaging (MI) images of compromised tissue after surgery and before necrosis is visible to the naked eye.

Each of the additional features and teachings disclosed below can be utilized separately or in conjunction with other features and teachings to provide systems and methods directed to the assessment of tissue vascular health utilizing structured light illumination methods to determine subsurface tissue properties. Such structured light illumination methods may include, but are not limited to, e.g., Modulated Imaging (MI), Spatial Frequency Domain Imaging (SFDI), and the like.

Embodiments of the present disclosure integrate hardware and software solutions to minimize motion artifacts, reduce imaging times, reduce cost, improve light throughput, co-register data, and increase field of view (FOV). Embodiments of the present disclosure acquire snapshot MI data of dorsal and plantar sides of a foot in under 1 second for each side, resulting in a 20× improvement in imaging times coupled with a 50% increase in FOV.

Embodiments of the present disclosure enable mining of historical and new data to develop staging and prediction algorithms based on global and local changes in MI biometrics, including hemoglobin concentration and saturation, water content indicative of edema, and tissue scattering coefficient indicative of structure changes that may compromise healing or cause ulceration.

Representative examples of the embodiments described herein, which examples utilize many of these additional features and teachings both separately and in combination, will now be described in further detail with reference to the attached drawings. This detailed description is merely intended to teach a person of skill in the art further details for practicing preferred aspects of the present teachings and is not intended to limit the scope of the invention. Therefore, combinations of features and steps disclosed in the following detail description may not be necessary to practice the invention in the broadest sense, and are instead taught merely to particularly describe representative examples of the present teachings.

Moreover, the various features of the representative examples and the dependent claims may be combined in ways that are not specifically and explicitly enumerated in order to provide additional useful embodiments of the present teachings. In addition, it is expressly noted that all features disclosed in the description and/or the claims are intended to be disclosed separately and independently from each other for the purpose of original disclosure, as well as for the purpose of restricting the claimed subject matter independent of the compositions of the features in the embodiments and/or the claims. It is also expressly noted that all value ranges or indications of groups of entities disclose every possible intermediate value or intermediate entity for the purpose of original disclosure, as well as for the purpose of restricting the claimed subject matter.

In certain embodiments of the present disclosure, an optical measurement device includes a light source with one or more wavelengths, configured to illuminate an area of tissue, a detector configured to capture the light reflecting from the tissue at the one or more illumination wavelengths, a processor configured to compute, based on the detected signal, one or more estimates of tissue vascular health, and a display or communication device (e.g., electronic data transfer) configured to store or report the tissue vascular health. The estimate of tissue vascular health may include one or more estimates of tissue health and/or risk of tissue injury, based on the concentration, lateral distribution, and/or depth distribution of one or more subsurface tissue constituents exhibiting optical absorption and/or scattering contrast (e.g., blood concentration, blood oxygenation, water/hydration, collagen, lipids, exogenous agents), and/or based on an estimate of vasomotor regulation derived from the one or more tissue constituents exhibiting absorption and/or scattering contrast.

In operation, tissue vascular health may be assessed with a single time point capture. To accomplish such assessment, an area of tissue is illuminated by a light source with one or more wavelengths, light reflecting from the tissue at the one or more illumination wavelengths, estimates of tissue vascular health are computed from the detected or captured light signals, and the computed estimate of tissue vascular health is displayed for review.

The source of the optical measurement device may be configured to create at least one spatially-structured light pattern over the tissue surface. The detector may be a 2D imaging detector array (such as, e.g., a CCD/CMOS camera). The detector may be a single-element detector (such as, e.g., a photodiode or an optical fiber relay to a detection system). Alternatively, multiple single-element detectors may be configured to collect reflected light from multiple tissue locations. The display may be an interactive touch-screen device, tablet, or digital phone. The optical measurement device may be configured to interface with a computer system, tablet, or digital phone with a wired or wireless connection. Exemplary detection systems are described in U.S. Pat. Nos. 8,892,192 and 9,220,412, which are incorporated herein by reference as if set forth in full.

In operation, a diagnosis of tissue health and/or risk is generated, and a recommendation of a therapy, treatment, product, or behavioral change is provided.

Modulated imaging (MI), is a novel non-contact optical imaging technology that was invented at the Beckman Laster Institute. MI has the unique capability of spatially resolving optical absorption and scattering parameters, allowing wide-field quantitative mapping of tissue optical properties. By separating and quantifying the multi-spectral absorption and scattering optical properties, MI removes the cross talk in reflectivity changes resulting from physically distinct contrast mechanisms, and provides a more direct assessment of tissue state and predictive power via derivation of physiologically relevant parameters.

While compatible with temporally-modulated photon migration methods, MI alternatively uses spatially-modulated illumination for imaging of tissue constituents. Periodic illumination patterns of various spatial frequencies are projected over a large (many $cm^2$) area of a sample. The reflected image differs from the illumination pattern due to the optical property characteristics of the sample. Typically, sine-wave illumination patterns are used. The demodulation of these spatially-modulated waves characterizes the sample modulation transfer function (MTF), which embodies the optical property information. Accelerated Monte Carlo-based analysis of MTF data results in 2D maps of the quantitative absorption (pa) and reduced scattering ($\mu_s'$) optical properties. Mapping the absorption coefficient at multiple wavelengths enables quantitative spectroscopy of tissue chromophores such as oxy- and deoxy-hemoglobin and water ($ctO_2Hb$, $ctHHb$, and $ctH_2O$) and derived physiology parameters such as tissue oxygen saturation and blood volume (stO2 and ctTHb). The spatially-varying phase can also be measured, yielding topological surface information. This enables visualization of the 3D tissue profile, as well as calibration data for accommodating curved surfaces in the analysis.

FIGS. 1A and 1B show an example of a tissue that on visual inspection appears healthy but is clearly compromised according to modulated imaging (MI)-derived wide-field maps. The image on the right shows the resulting tissue failure.

Figure 2C:
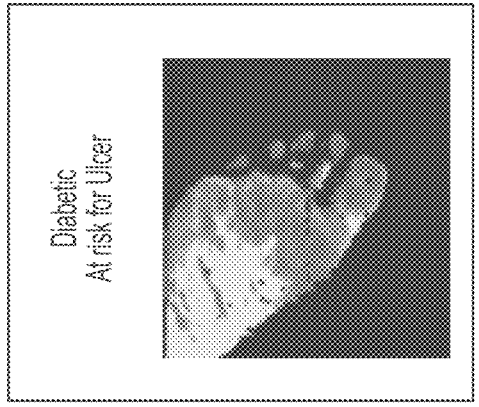
FIGS. 2A, 2B and 2C illustrate modulated imaging (MI) images of a non-diabetic healthy foot, a diabetic with a healthy foot, and a diabetic with a high risk of ulcer formation.
Figure 2B:
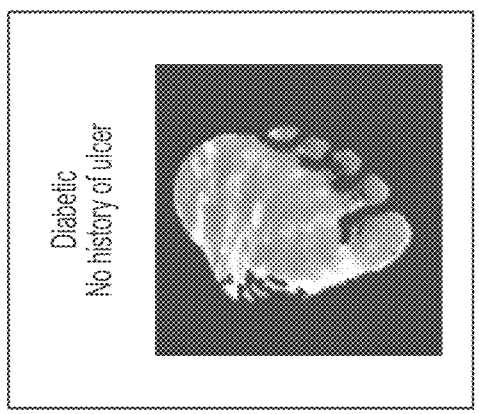
Figure 2A:
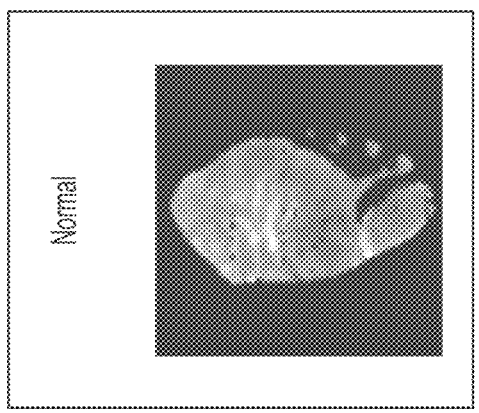

FIGS. 2A and 2B illustrate modulated imaging (MI) images of a non-diabetic healthy foot (left) a diabetic with a healthy foot (center) and a diabetic with a high risk of ulcer formation (right).

Figure 3:
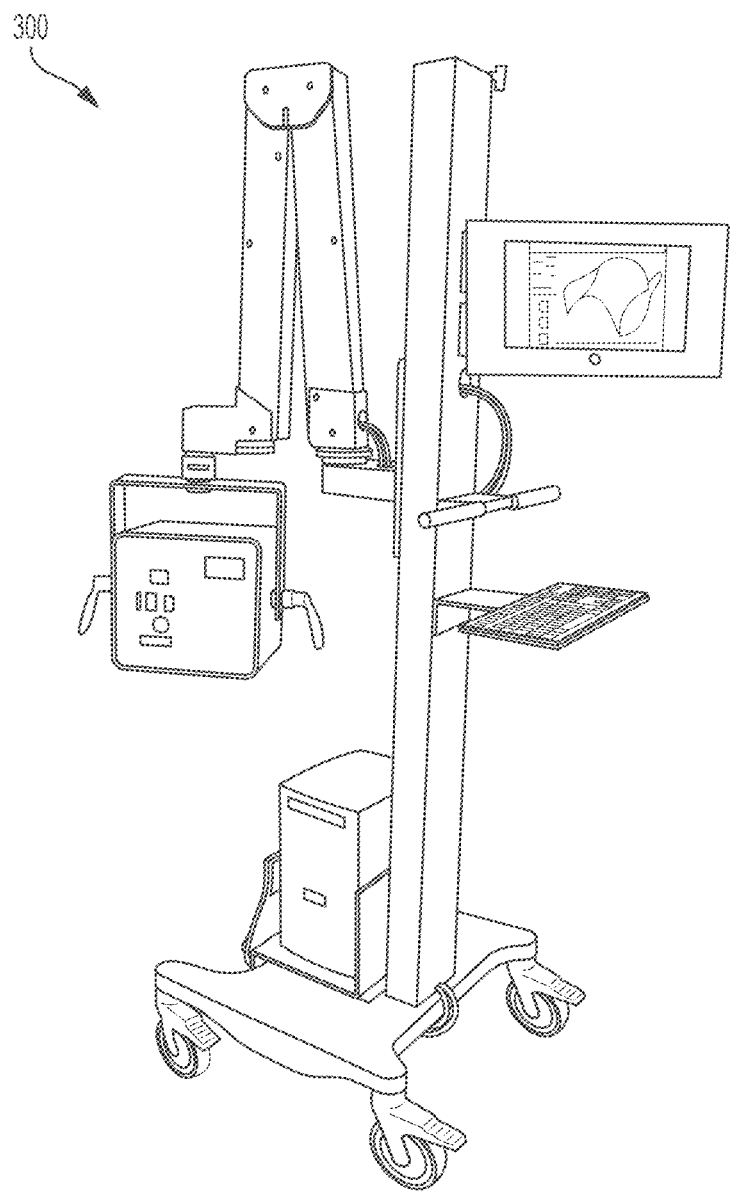
FIG. 3 illustrates an example embodiment of an optical measurement device for use with embodiments of the present disclosure.

FIG. 3 illustrates an example embodiment of an optical measurement device for use with embodiments of the present disclosure. The exemplary optical measurement device 300 is capable of measuring absorption and scattering maps using eleven LED wavelengths spanning the visible to NIR range (400-980 nm) over large fields of view (15×20 cm). These wavelengths are selected for their sensitivity for quantitation of melanin, deoxygenated hemoglobin, oxy-hemoglobin, and water. Microcontroller electronics synchronize with LED pulses with DMD projection and camera acquisition, enabling rapid image sequence capture of all spatial patterns and wavelengths. The device 300 is capable of acquiring data with ~15 ms integration time per image. A typical sequence of images (11 wavelengths, 5 spatial frequencies ~165 images) take a total of ~20 seconds to acquire data and is reducible to is for DFU. The device 300 includes simultaneous collection of surface topology measurements and tissue color (RGB) photographs for calibrated, color-balanced illumination, enabling a standardized method of comparing MI results with visual clinical impression. The device 300 can also be used in IACUC and IRB-approved studies studying applications including burn wounds, skin flaps, decubitus ulcers, cancer, and dermatology.

Figure 4A:
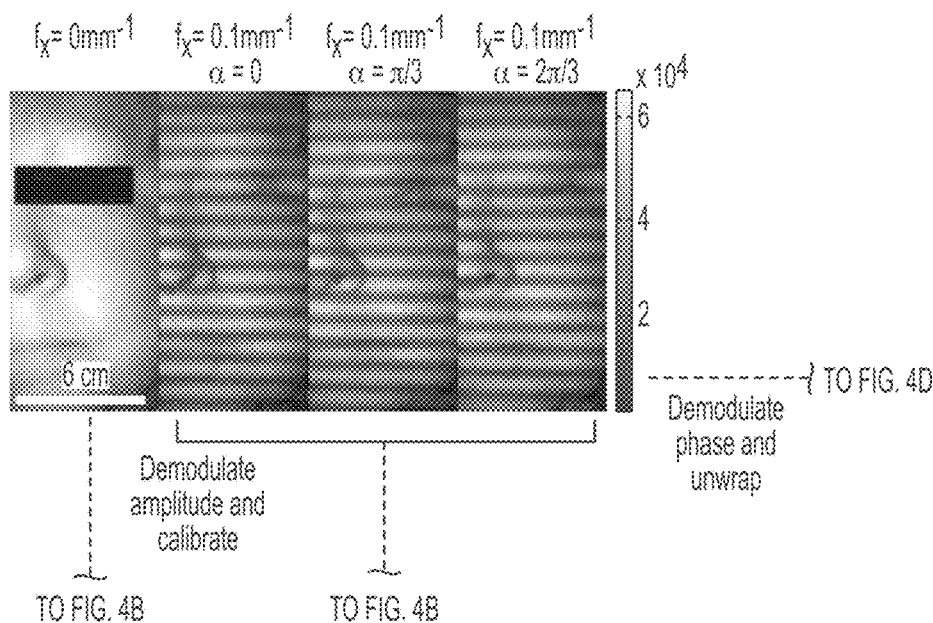
FIGS. 4A, 4B, 4C and 4D illustrate a flowchart of modulated imaging (MI) data for use with embodiments of the present disclosure.
Figure 4B:
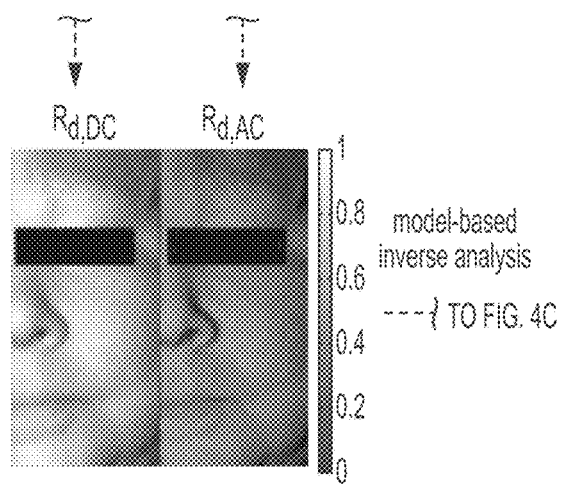
Figure 4D:
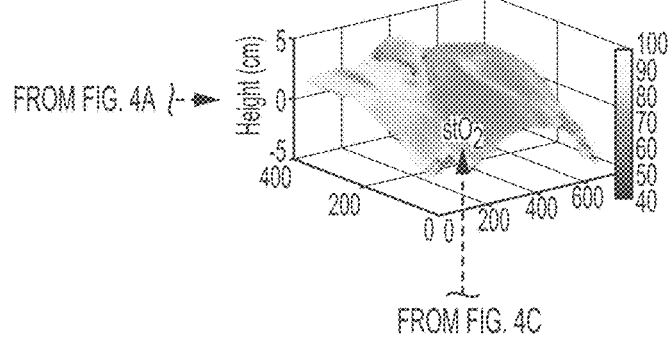
Figure 4C:
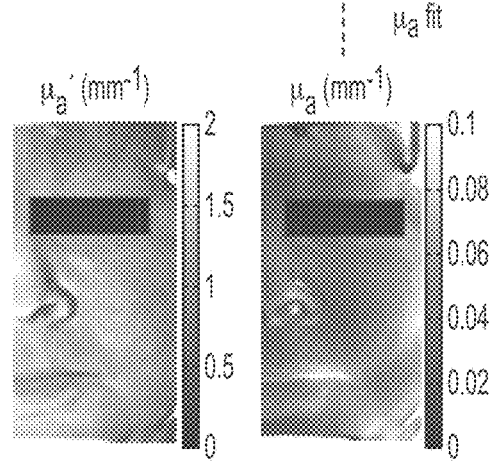

FIGS. 4A, 4B, 4C and 4D illustrate a flowchart of modulated imaging (MI) data processing for use with embodiments of the present disclosure. In FIG. 4A, modulated intensity patterns are projected onto the surface at each frequency (three phase images per frequency). In FIG. 4B, the patterns are amplitude demodulated and calibrated. In FIG. 4C, the patterns are fit to a multi-frequency model to determine optical properties. In FIG. 4D, separately phase demodulation provides information on tissue height, which can be used for both curvature calibration and visualization. Data are processed separately for each pixel, generating spatial maps of optical properties.

Figures 5A, 5B:
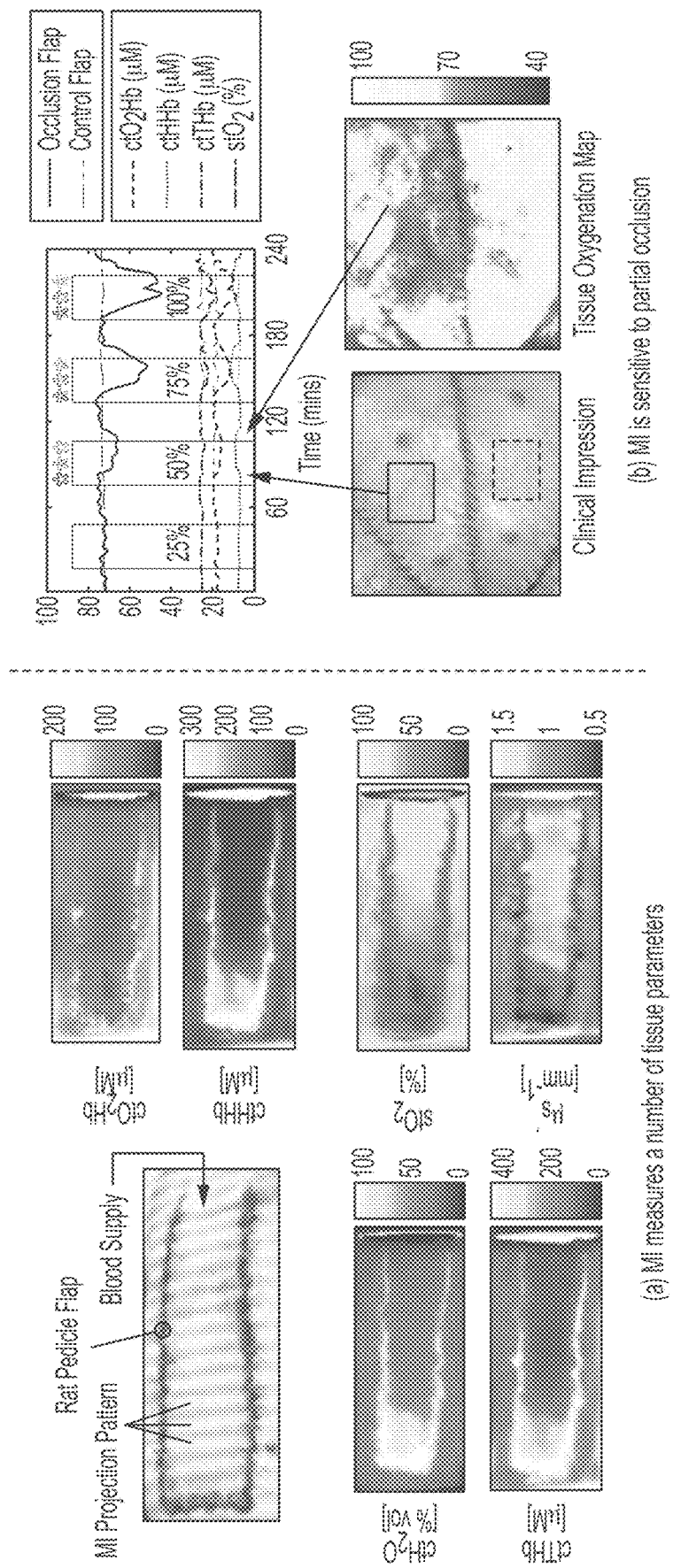
FIGS. 5A and 5B illustrate measurements of gradient changes in perfusion, according to embodiments of the present disclosure.

FIGS. 5A and 5B illustrate measurements of gradient changes in perfusion, according to embodiments of the present disclosure. In FIGS. 5A and 5B, a rodent McFarlane dorsal pedicle flap model was used to demonstrate the ability to measure gradient changes in perfusion. In FIG. 5A, MI measured decreased oxygenation and increased blood pooling at the distal end of the flap where flow was most compromised. Additionally, an increase in water content (i.e., edema) and decrease in reduced scattering (i.e., early necrosis) are observed at the distal end of the flap. MI measures of scattering and tissue water content provide novel measures of tissue health and improve accuracy of tissue hemoglobin and oxygen saturation by removing crosstalk. In FIG. 5B, early detection of compromised perfusion in flaps using a porcine model are demonstrated. Flap perfusion was isolated to a single group of arteries and vein for each flap and inflow/outflow were systematically controlled with an implanted occlusion balloon and a flow sensor. MI parameters demonstrated sensitivity to small changes in vascular inflow during a series of controlled levels of arterial occlusion. MI detected changes in flow prior to clinical impression, as recorded by calibrated color photography. MI also revealed perfusion for partial occlusions varied spatially. MI $stO_2$ showed strong correlation with simultaneous measurements with an FDA-cleared NIRS tissue oximeter. MI was able to differentiate between arterial and venous congestion based on oxy- and deoxy time traces.

Figures 6A, 6B:
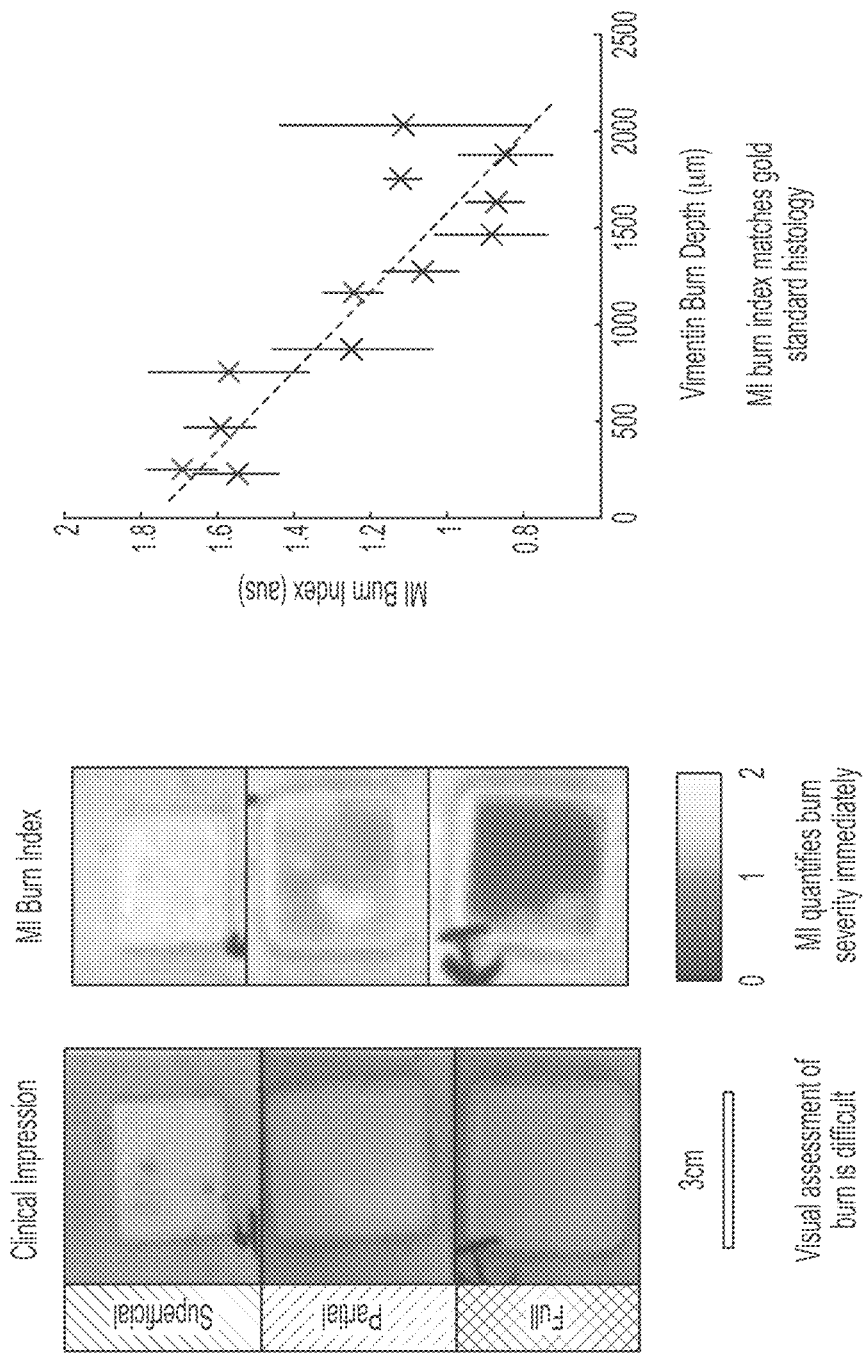
FIGS. 6A and 6B illustrate derived SFDI outputs used to develop a burn index map, according to embodiments of the present disclosure.

FIGS. 6A and 6B illustrate derived SFDI outputs used to develop a burn index map, according to embodiments of the present disclosure. In FIGS. 6A and 6B, multiple burn wounds of three severities (superficial partial thickness, deep partial thickness and full thickness) are shown in a porcine model over the course of 72 hours. Differential contrast was observed for the many parameters that MI measures ($ctO_2Hb$, $ctHHb$, $stO_2$, scattering). Functional parameters such as $stO_2$ and ctHHB evolved over the course of 72 hours and were statistically differentiable from each other ($p<0.01$) at this time. The reduced scattering contrast was a much more stable measurement. A reduction in scattering was measured that correlated with burn depth as measured by histology ($r2=0.94$). This scattering is believed to be sensitive to the phase change of the collagen fibrils as they are thermally denatured and broken down. Derived SFDI outputs (absorption and scattering) were combined to create a burn index map that correlates with burn depth. A burn index can predict burn wound outcome and provide early treatment guidance to clinicians (i.e., self-healing vs. graft).

Figures 7A, 7B:
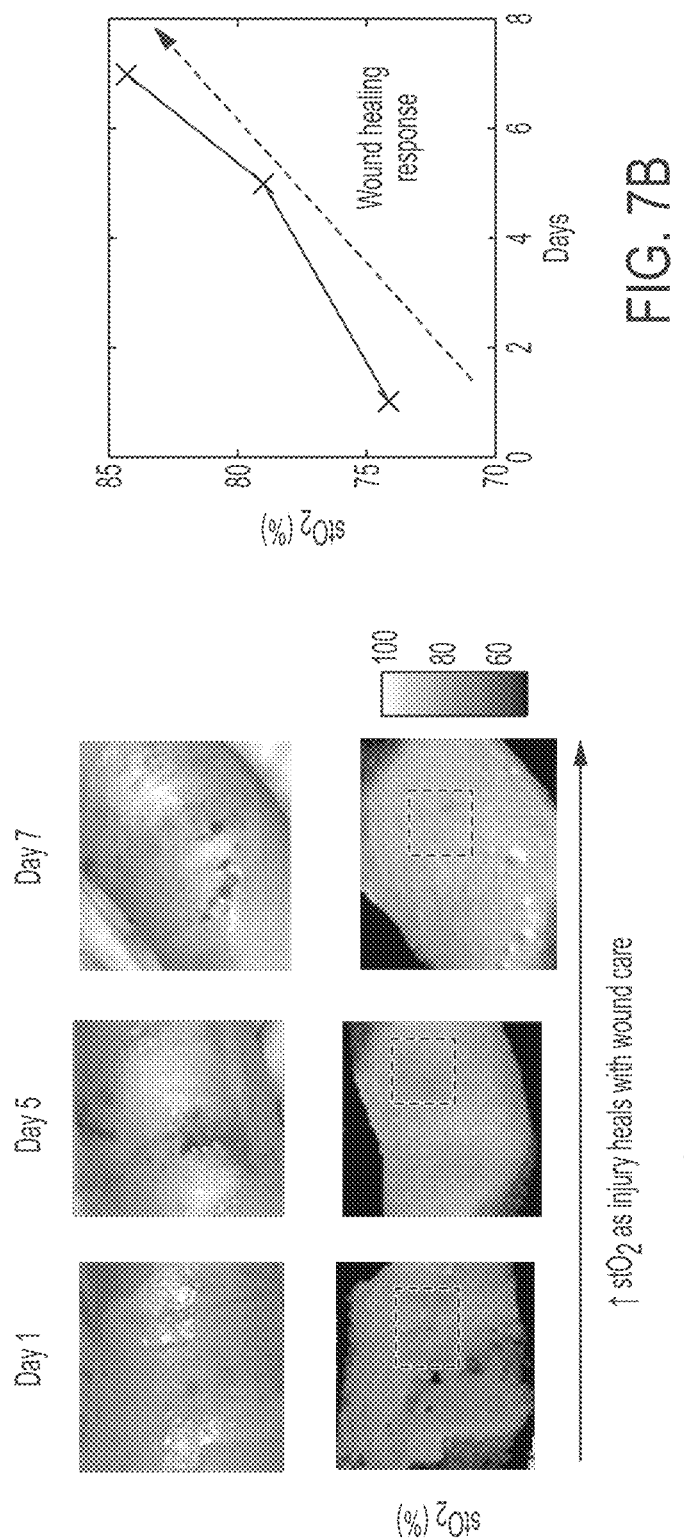
FIGS. 7A and 7B illustrate time course measurements of a burn, according to embodiments of the present disclosure.

FIGS. 7A and 7B illustrate time course measurements of a burn, according to embodiments of the present disclosure. In the superficial thickness wound of FIG. 7A, a steady increase in oxygen saturation over time is observed in the burn wound. This is a strong indicator of the tissue healing process in burn injuries and is linked to eventual outcome.

Figures 8A, 8B, 8C:
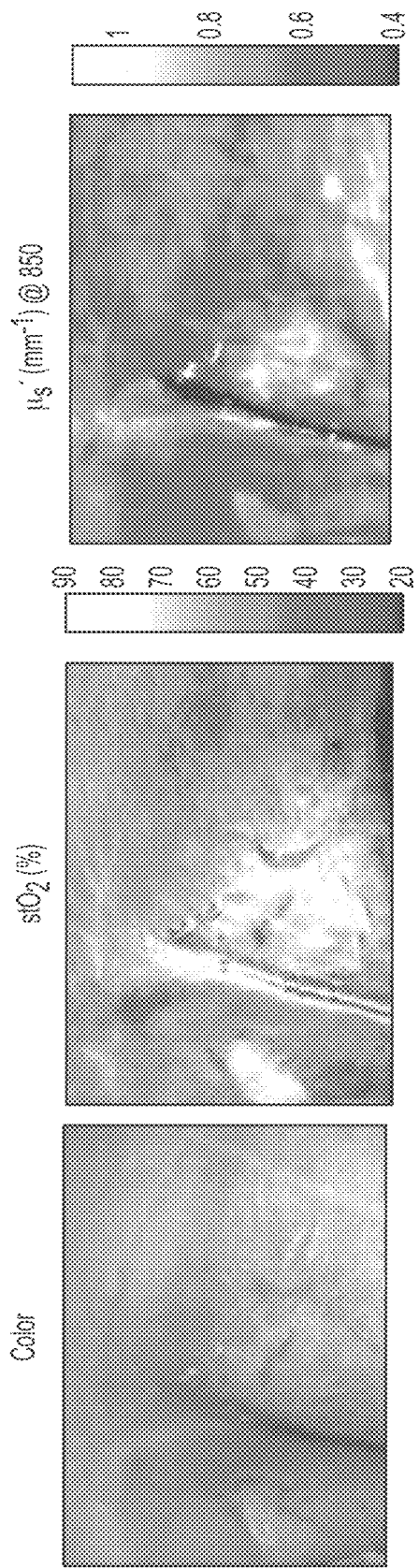
FIGS. 8A, 8B and 8C illustrate a photograph of an unstageable decubitus ulcer and MI derived maps of tissue oxygenation and scattering, according to embodiments of the present disclosure.

FIGS. 8A, 8B and 8C illustrate photographs of an unstageable decubitus ulcer and MI derived maps of tissue oxygenation and scattering, according to embodiments of the present disclosure. A clinically unstageable decubitus ulcer in a 69-year-old patient is shown in FIGS. 8A, 8B and 8C. A color photograph (FIG. 8A) is shown and compared to a MI-derived map of deep-tissue $stO_2$ (FIG. 8B). The color photo indicates an ambiguous, pink state with ruptured epidermis. The oxygenation map indicates a more specific diffuse zone of hyper-saturation extending beyond the visible dermal damage to the periwound area, potentially indicating the extent of inflammation in a wound-healing response. A co-located but distinctly smaller zone of increased scattering (FIG. 8C) may indicate matrix structural modifications at the center of the wound area from tissue repair (granulation tissue has been found to have a high scattering coefficient).

Figure 9:
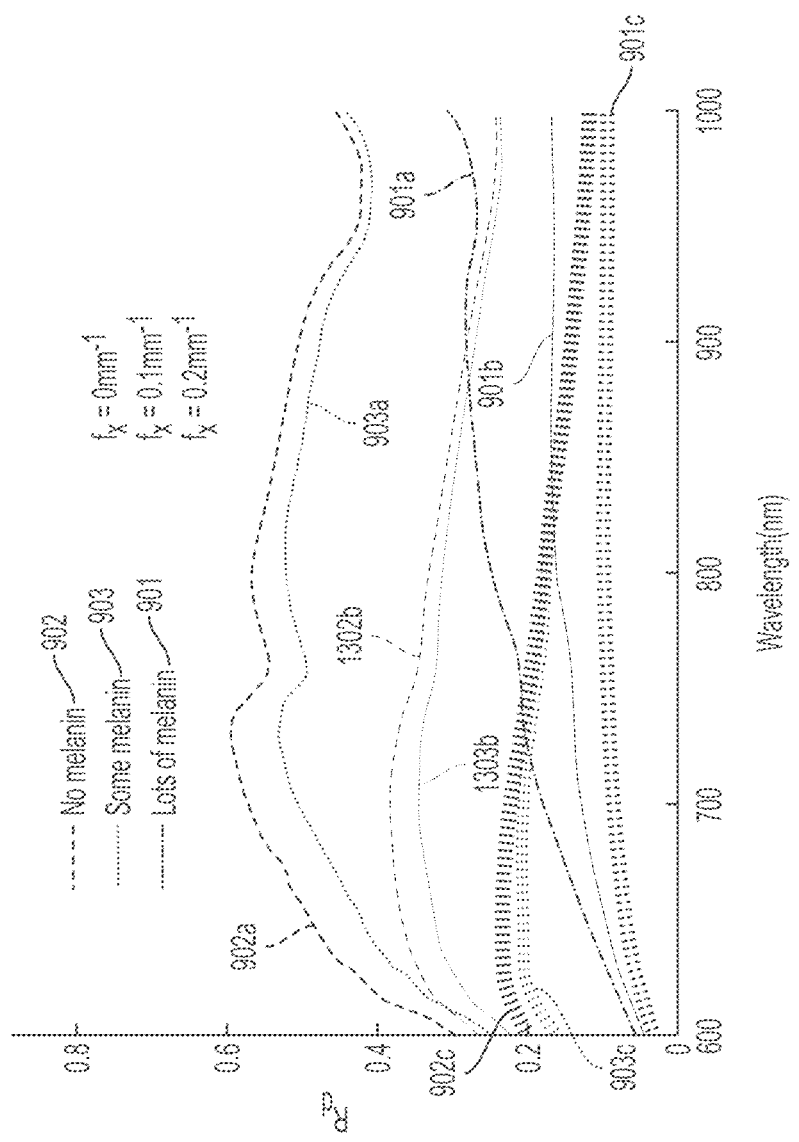
FIG. 9 illustrates examples of SFD spectra for varying melanin concentrations and spatial frequencies.

FIG. 9 illustrates examples of SFD spectra for varying melanin concentrations and spatial frequencies. Development of advanced multi-layer multi-spectral models using MI resulted in the ability to generate forward simulated MI spectra for multiple skin types and perform simulations to determine sensitivities of the recovered MI signals to chromophore changes in each layer.

MI data has led to development of a brand-new spatial frequency domain (SFD) Monte Carlo simulation code capable of directly simulating Modulated Imaging SFD data for multi-layered tissues. This code allows "native" frequency-domain tallies of exiting photons, and removes significant aliasing problems associated with traditional methods relying on Fourier-transformation of real-domain (e.g., R(ρ) or "source-detector") data. Using a combination of White Monte Carlo (rapid adjustment of tissue absorption), spatial rescaling (rapid adjustment of tissue scattering and spatial frequency), and lookup tables, a novel method of accelerating the simulations has been developed. The end result is an algorithm that takes only ~1 ms per curve to calculate tissue reflectance from an arbitrary number of layers, layer thicknesses, and layer optical properties. A "classic" Monte Carlo simulation with the same data fidelity would require 2.5 hours, representing a speedup factor of approximately $10^8$.

In FIG. 9, SFD spectra is shown for a concentration of no melanin (902, lines 902a, 902b, 902c), some melanin (903, lines 903a, 903b, 903c) and lots of melanin (901, lines 901a, 901b, 901c). Based on these results, the internal light penetration and sensitivities of the detected photons to changes of chromophores were determined in each layer including epidermis, dermis, and sub-cutaneous tissues.

Figure 10B:
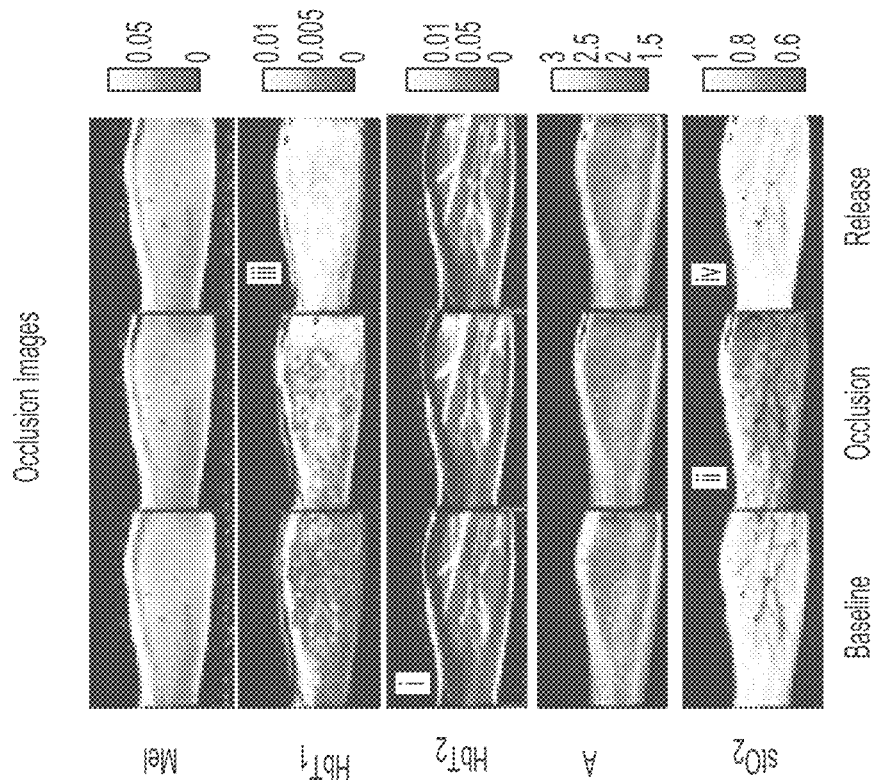
FIGS. 10A and 10B illustrate a three layer geometry developed for skin imaging, for use with embodiments of the present disclosure.
Figure 10A:
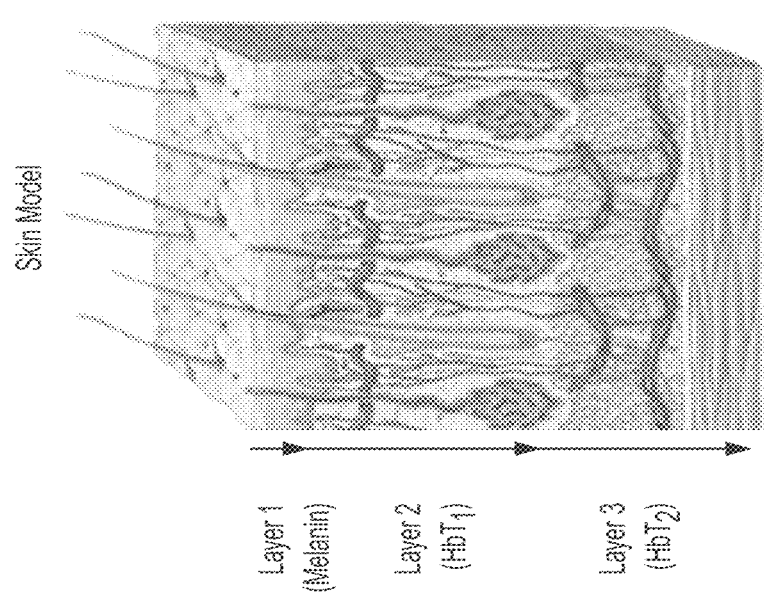

FIGS. 10A and 10B illustrate a three layer geometry developed for skin imaging, according to embodiments of the present disclosure. Previous publications have validated depth-homogeneous sampling for dynamic $stO_2$ measurements; however, melanin remained a confounding factor when analyzing skin data. In addition, superficial hemoglobin changes (e.g., hyperemia in the papillary dermis) would appear washed out with very low contrast. In FIGS. 10A and 10B, which illustrate a 3-layer geometry developed for skin aging using MI, light transport in the visible and near infrared regime were modeled using Monte Carlo models of light transport in the Spatial Frequency Domain. Validated transport computational codes were adopted from the Virtual Photonics Technology Initiative, an open-source software project for biophotonics at UC Irvine. In FIG. 10A, a new three layer skin model is applied to an arteriovenous arm-cuff occlusion measurement. In FIG. 10B, recovered MI parameters highlight differentiation between superficial and (i) deep hemoglobin. During occlusion, $stO_2$ is reduced dramatically and then upon release recovers with an (iii, iv) influx of oxygenated hemoglobin during reactive hyperemia.

Figures 11A, 11B:
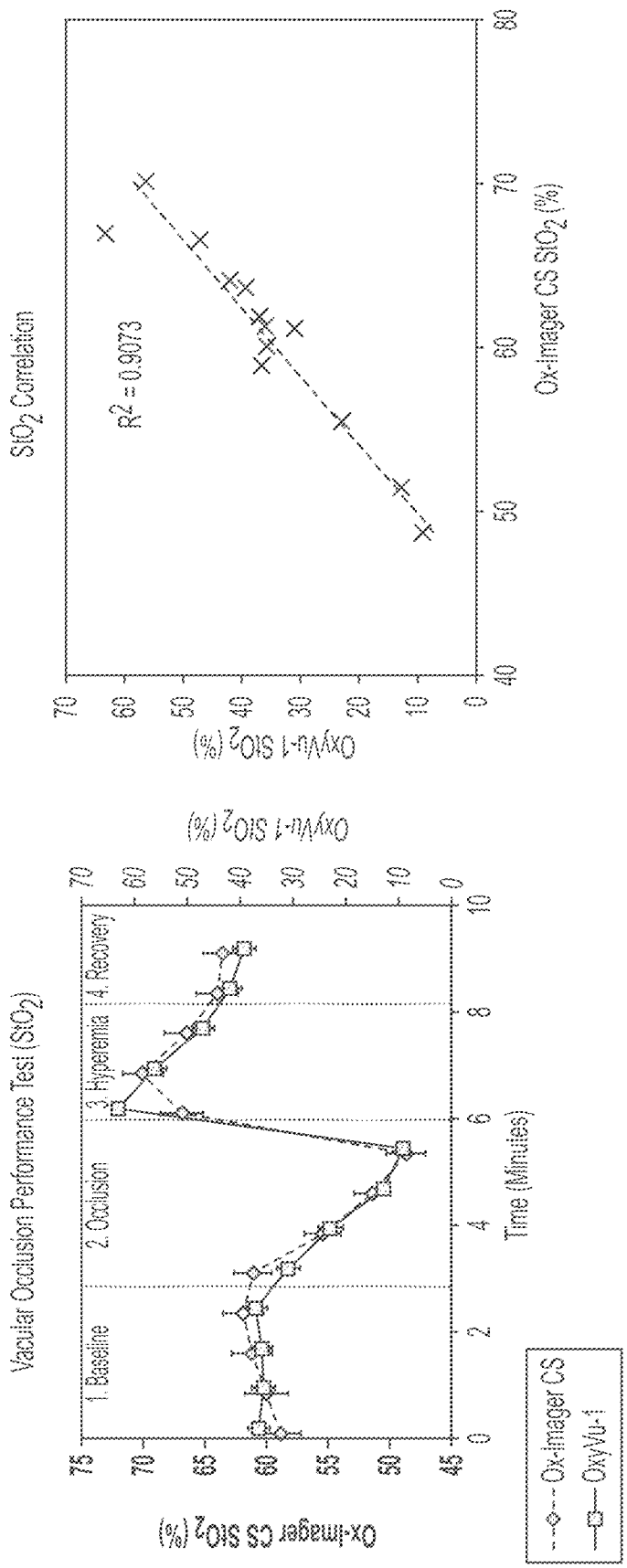
FIGS. 11A and 11B illustrate a correlation of mean values and standard error of StO2 measured by Ox-Imager CS and OxyVu-1.

FIGS. 11A and 11B illustrate a correlation of mean values and standard error of $StO_2$ measured by Ox-Imager CS and OxyVu-1. Subjects of skin types (Fitzpatrick I-VI) were occluded and chromophores were measured at baseline, during occlusion and release for both the Ox-Imager and a FDA predicate device, the HyperMed OxyVu-1. Measured tissue oxygenation shows significantly reduced oxygen saturation during cuff occlusion, and hyperemia upon release. Although, absolute values are different between devices, that characteristic shape of a vascular occlusion test between the systems demonstrate a strong correlation ($r^2>0.9$). The difference in absolute values is due to deeper tissue penetration of the signals using the Ox-Imager system.

Figures 12A, 12B:
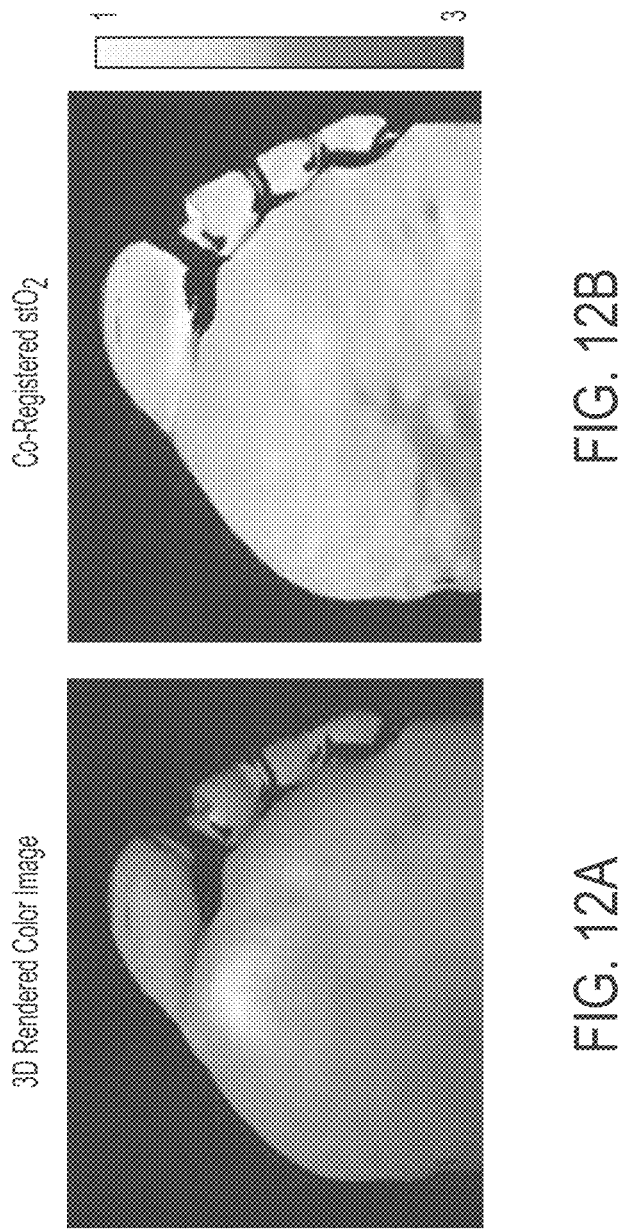
FIGS. 12A and 12B illustrate 3D renderings of a foot with core-registered tissue oxygen saturation map.

FIGS. 12A and 12B illustrate 3D renderings of a foot with core-registered tissue oxygen saturation map. Multi-height correction is a critical component of MI data analysis. The complex geometry of feet can affect the interpretation of results if this is not dealt with in an appropriate manner. Structured illumination is used to reconstruct tissue height and apply corrections to the data to improve accuracy.

Figure 13:
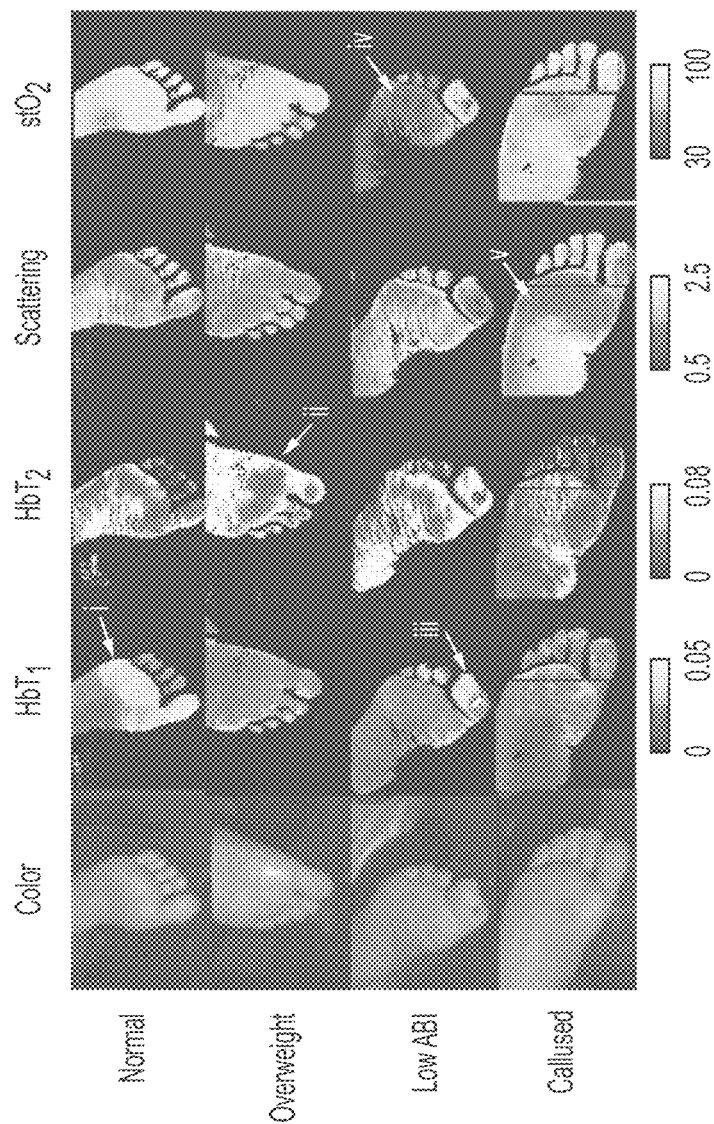
FIG. 13 illustrates a collage of preliminary foot data showing a variety of hemoglobin and oxygen saturation levels.

FIG. 13 illustrates a collage of preliminary foot data showing a variety of hemoglobin and oxygen saturation levels. For a normal foot, elevated superficial hemoglobin is observed in the pads (i) of the feet along with homogeneous saturation across the surface of the foot. In an overweight diabetic patent, decreased levels of deep hemoglobin (ii) are observed at the pressure points in the pads of the feet and high levels in the arch of the foot. For a patient with a low ABI (ABI=0.70), elevated levels of deep hemoglobin are observed throughout the foot with low oxygenation (iv)—except for a small area that has an ulcer—which has elevated superficial hemoglobin (iii) and oxygen saturation in the peri-wound. In the case of a callused foot, a decrease in scattering (v) is observed compared to surrounding area in the callused area—a possible result of epidermal thickening.

Figure 14B:
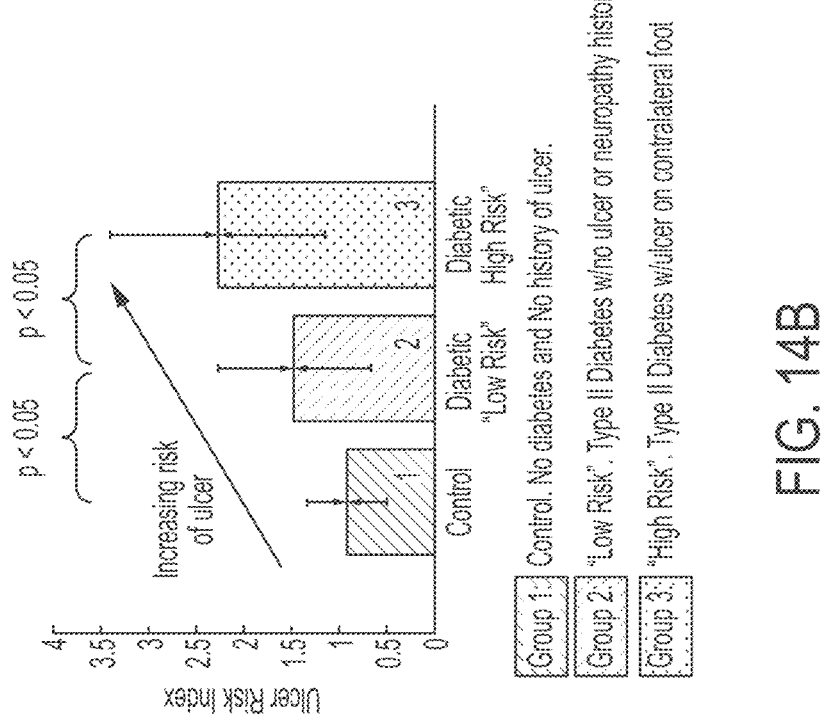
FIGS. 14A and 14B illustrate the use of MI biometrics to create an ulcer risk index that stratifies ulcer risk in subjects.
Figure 14A:
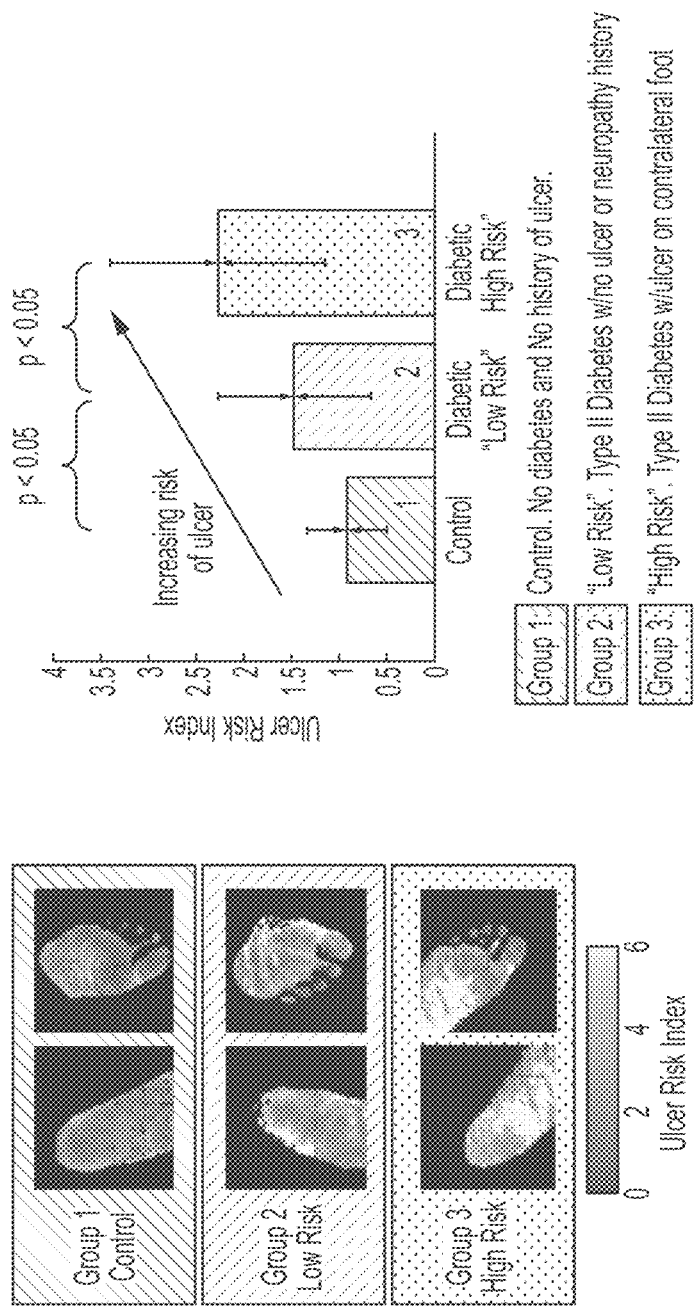

FIGS. 14A and 14B illustrate the use of MI biometrics to create an ulcer risk index that stratifies ulcer risk in subjects. Imaged feet were divided into 3 cohorts: 1) a control group with no diabetes and no history of ulceration, 2) a "low risk" group with type II diabetes and no neuropathy and history of ulceration, and 3) "high risk" group with type II diabetes and ulcer on the contralateral foot. Using biometrics measured by the present system, an ulcer risk index was built based primarily on the ratio of superficial and deep hemoglobin. Initial analysis, shown in FIGS. 14A and 14B, shows that "high risk" cohort has elevated levels of deep hemoglobin and low levels of superficial hemoglobin—measurement outputs that are unique to the present system. It is believed that the pooling effect can be explained by poor vasomotor regulation of the capillaries likely caused by their health status. Furthermore, analysis shows that each cohort can be distinguished based on the distributed index value in the foot based on average image values.

Figure 15:
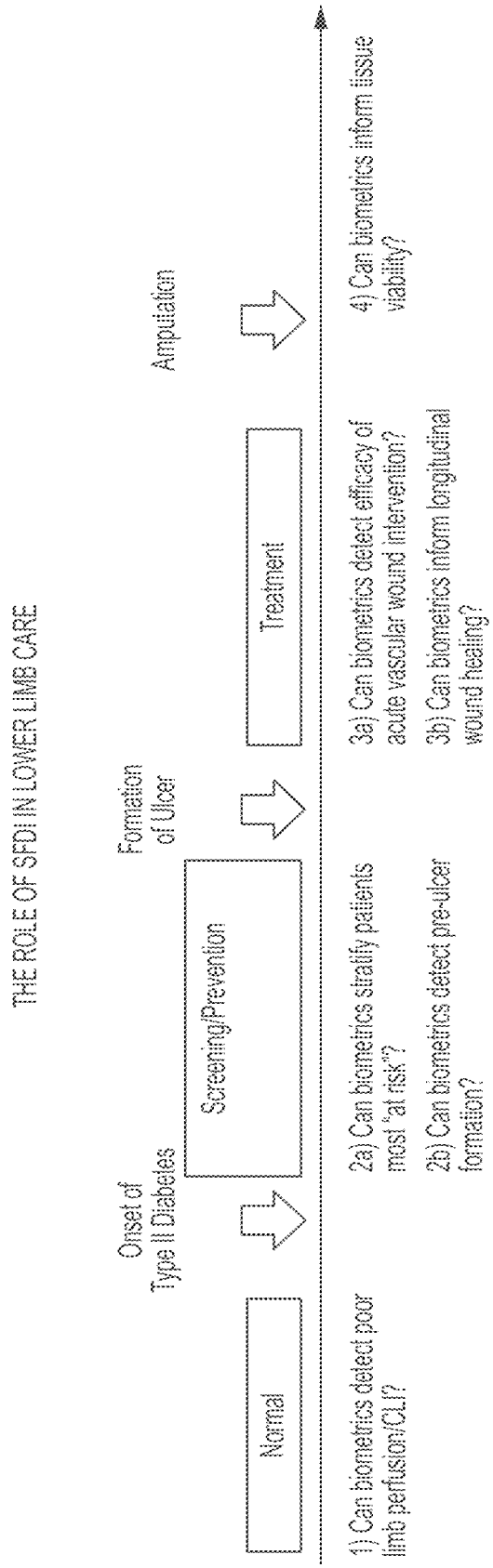
FIG. 15 illustrates a timeline of the role of SFDI in lower limb care, based on embodiments of the present disclosure.

FIG. 15 illustrates a timeline of the role of SFDI in lower limb care, based on embodiments of the present disclosure. Biometrics can be used from normal health situations to onset of type II diabetes, to formation of ulcer, to amputation phases. Biometrics aid in detection and inform therapies.

Figure 16B:
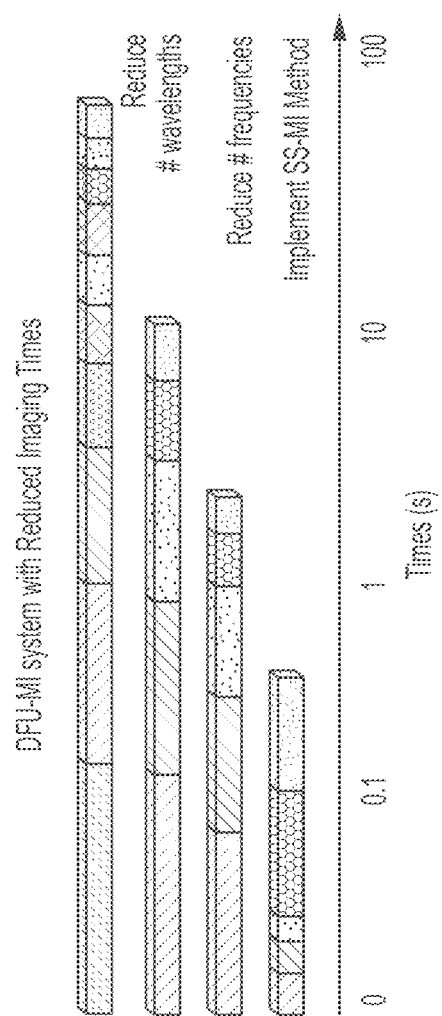
FIGS. 16A and 16B illustrate an expanded field of view and reduced imaging times according to embodiments of the present disclosure.
Figure 16A:
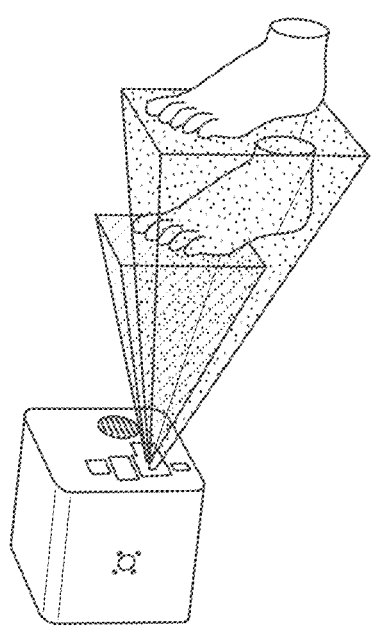

FIGS. 16A and 16A illustrate an expanded field of view and reduced imaging times according to embodiments of the present disclosure. In FIG. 16A, field of view is expanded from 20×15 cm to 50% larger to capture the entire foot in a single snapshot. A larger field of view puts greater demand on optical output and requires improvement in light throughput to keep exposure times short (<10 ms) so the measurements are insensitive to ambient room lights. For foot measurement, a 5-wavelength and single spatial frequency measurement is equivalent to a current 10 wavelength, 5 frequency measurement. Thus, more dies on the LED boards can be dedicated to the core wavelengths and structured and planar light can be combined to improve light throughput by a factor of 10. With this reduction, the total number of images in a sequence is 8 instead of 150. In FIG. 16B, step by step improvements are shown as well as how the changes reduce total imaging times 10-fold (from ~20 ms to <500 ms). These changes enable imaging in ambient room-light conditions, reduce the effects of motion artifacts, and improve long-term component reliability by reducing complexity.

Figure 17:
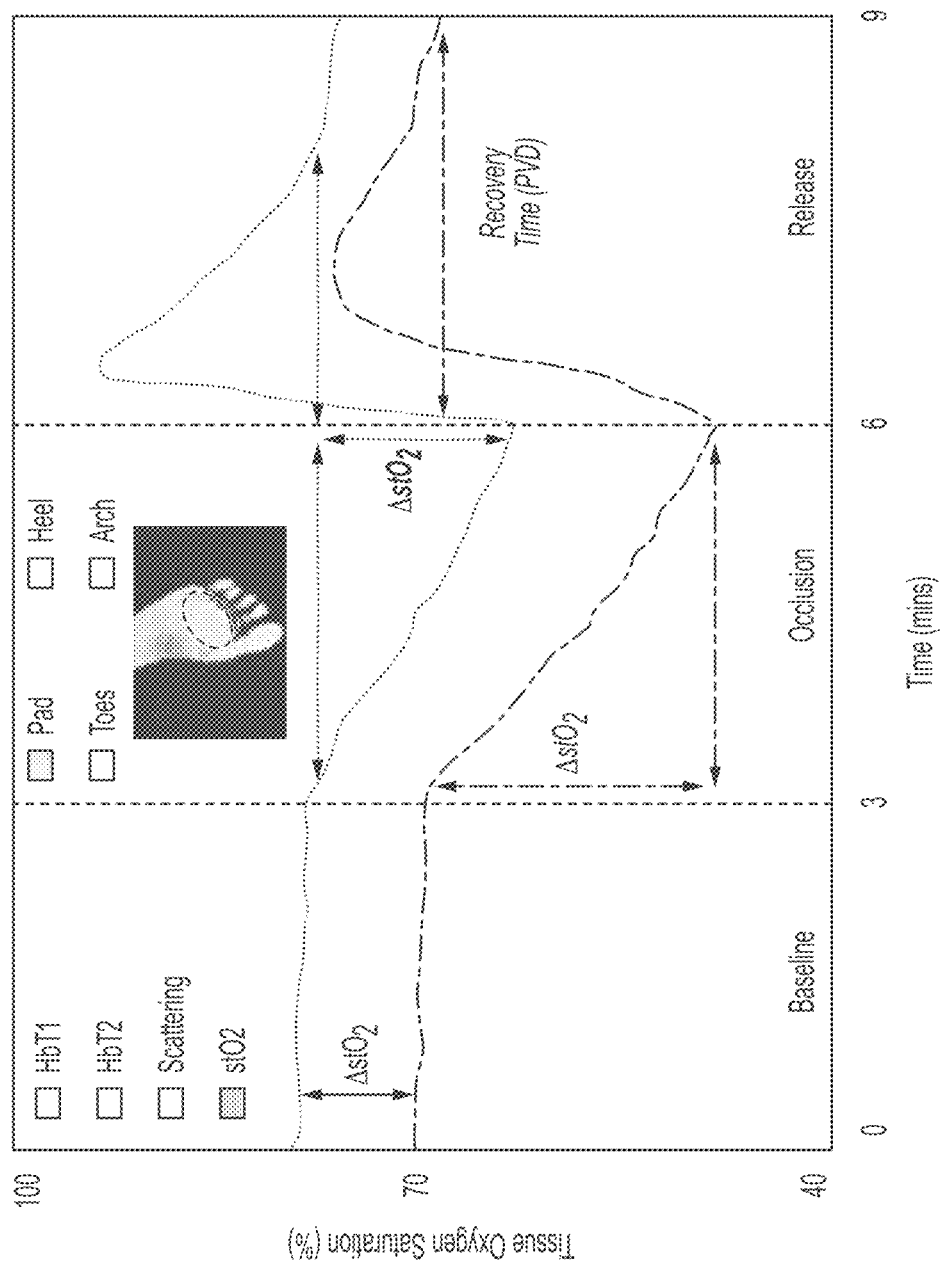
FIG. 17 illustrates a test results from a vascular reactivity study of a foot, according to embodiments of the present disclosure.

FIG. 17 illustrates test results from a vascular reactivity study of a foot, according to embodiments of the present disclosure. Dynamic measurements during ABI cuff challenge allow for the establishment of benchmarks for MI biometrics before, during, and after occlusion on the plantar side of the foot.

Figure 18:
FIG. 18 illustrates an example clinical assessment worksheet for use with embodiments of the present disclosure.

FIG. 18 illustrates an example clinical assessment worksheet for use with embodiments of the present disclosure. According to one assessment, 25 diabetic subjects with a history of an ulcer are following monthly for 12 months as indicated in table 1 below. The worksheet in FIG. 18 is used to record (i) the location of each previous ulceration, (ii) locations and reasons for other potential regions ono the subject's foot that may be at risk for ulceration in the next 6 months, and iii) risk category for the subject. H indicates a healed ulcer, P indicates a persistent ulcer, and D indicates danger of ulceration.

TABLE 1

Imaging session for 25 patient longitudinal study to assess DFU wound healing.

| | Visit | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Imaging | • | • | • | • | • | • | • | • | • | • | • | • |
| Assessment | • | • | • | • | • | • | • | • | • | • | • | • |

Figure 19A:
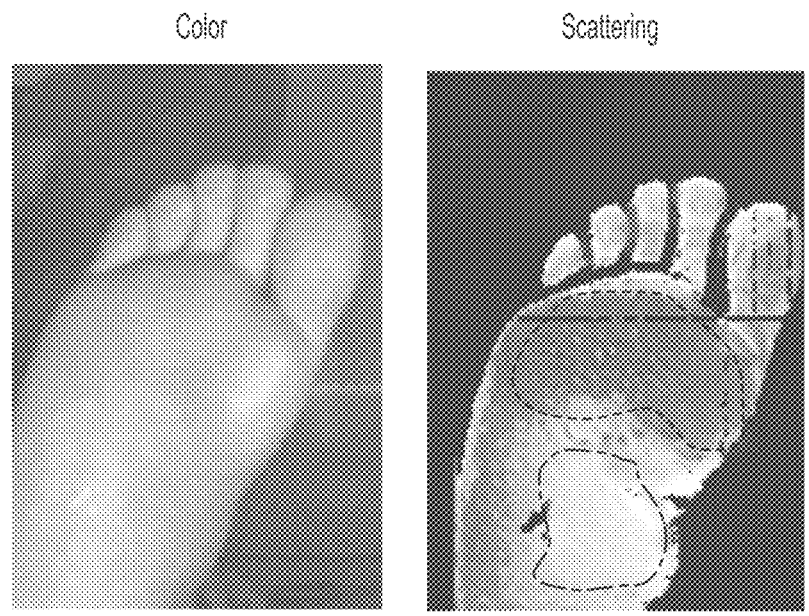
FIGS. 19A and 19B illustrate distribution of scattering in a callused foot, according to embodiments of the present disclosure.
Figure 19B:
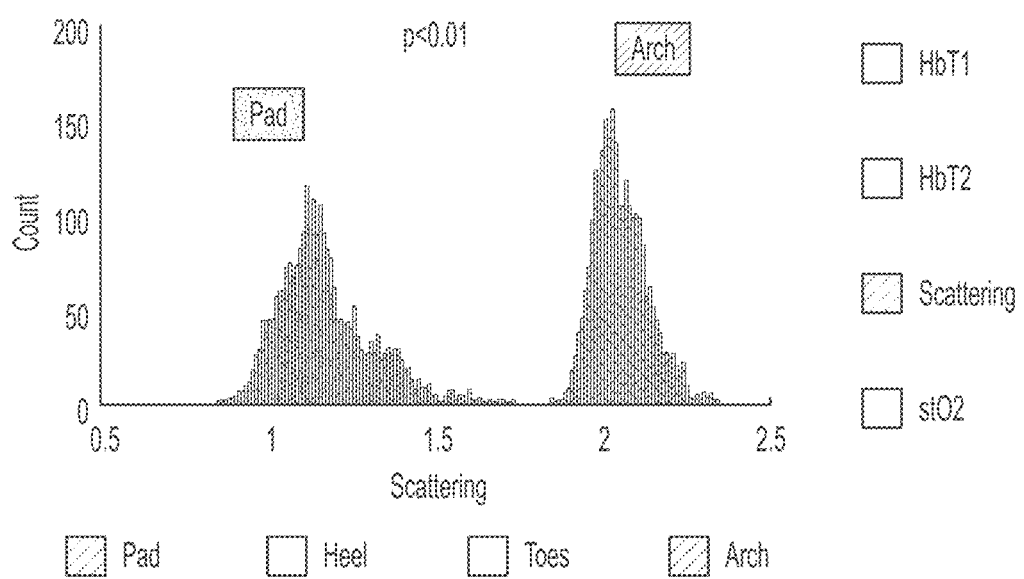

FIGS. 19A and 19B illustrate a distribution of scattering in a callused foot, according to embodiments of the present disclosure. The pads and arch of the plantar feet are identified, and a histogram distribution is generated of the scattering values. Distribution of scattering in the callused foot shows lower scattering at pressure points—perhaps an indication that a pre-ulcer callus has formed due to the pressure applied on the foot during gait. This type of analysis can be done for different areas of the foot as well as for each individual and combination of biometrics.

Cross-correlation maps are created to quantify the heterogeneity/homogeneity of MI foot biometrics as a novel tool to analyze distributions of MI biometrics in the foot. This analysis can be used for more powerful indices development. For example, region specific perfusion may be critical for better pre-ulcer detection due to pressure/callus formation. Or it may be critical when looking at vascular reactivity after an intervention in correlation to known angiosomes. A correlation between region-wise limb perfusion and ABI values is possible with the present system, overcoming the issue that there is no literature describing how a low ABI affects spatial distribution of perfusion to angiosomes in the foot.

Figure 20:
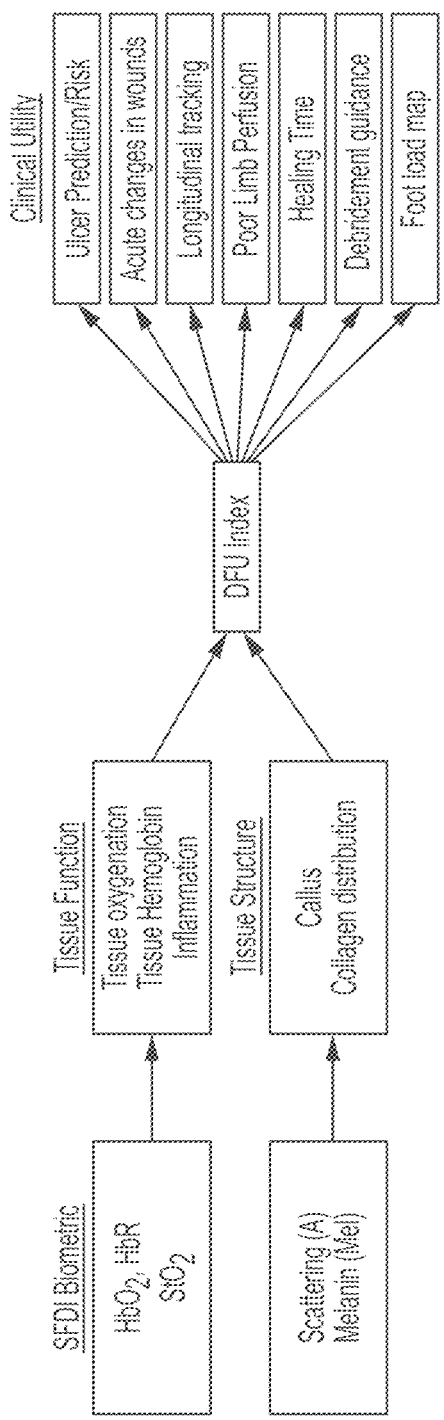
FIG. 20 illustrates building of an informative index based on embodiments of the present disclosure.

FIG. 20 illustrates building of an informative index based on embodiments of the present disclosure. A DFU index is developed based on MI-DFU biometrics that informs a clinician of a clinical outcome.

Figure 21:
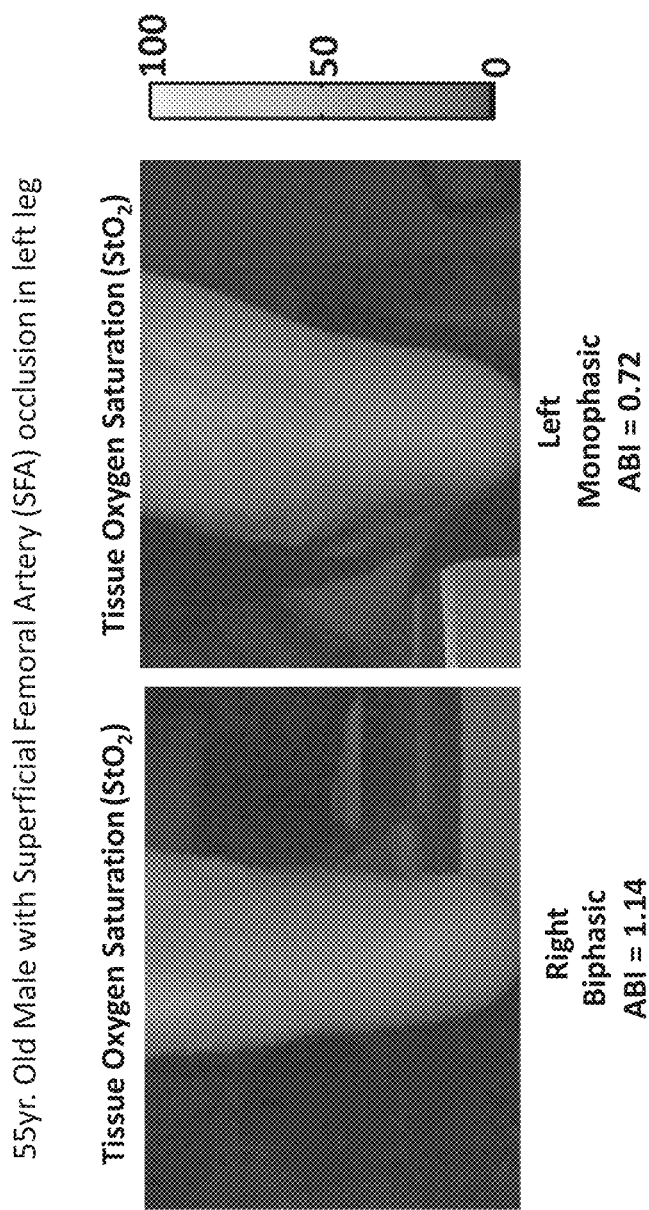
FIG. 21 illustrates images of vascular disease according to embodiments of the present disclosure.
Figure 22:
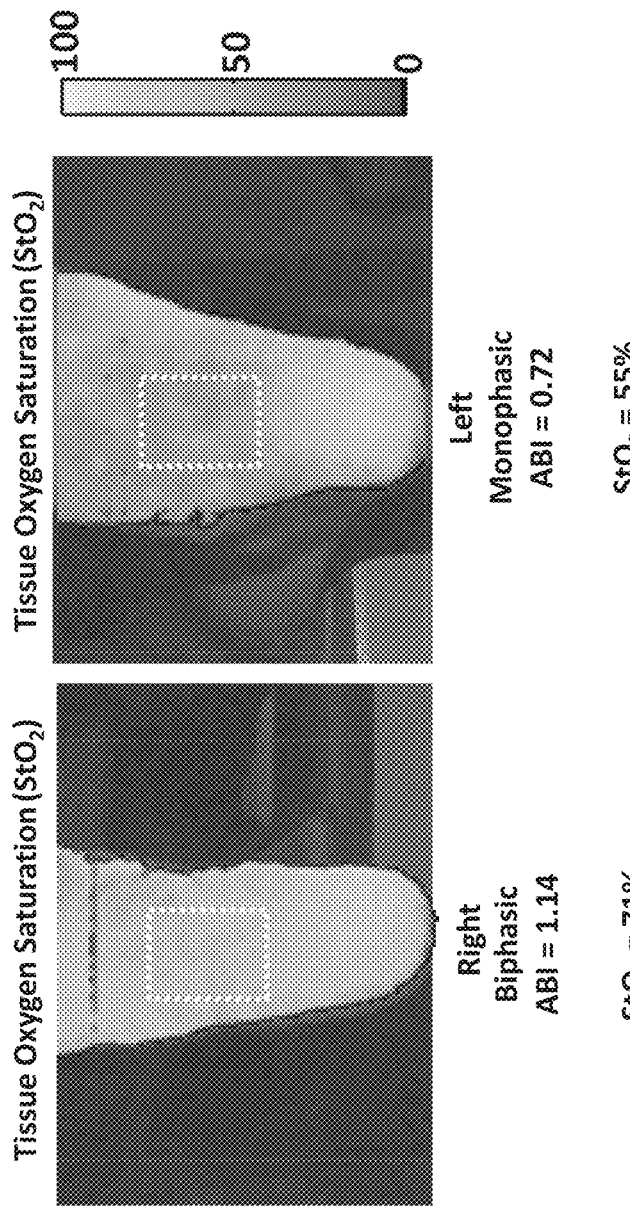
FIG. 22 illustrates images of vascular disease according to embodiments of the present disclosure.

FIGS. 21 and 22 illustrate images of vascular disease according to embodiments of the present disclosure. The present system is able to identify spatial features of the physiology which correspond to the location of angiosomes. FIGS. 21 and 22 show region-wise estimates of tissue oxygen saturation. Moreover, this has been correlated with ankle-brachial index (ABI) and digital waveform analysis for this subject. While the right foot in the figures has a biphasic waveform and an ABI of 1.14 and shows good oxygenation in the arch of the foot, the left foot in the figures has a monophasic waveform and an ABI of 0.72 and shows comparatively poor oxygenation in the arch of the foot compared to the heel region.

Figure 23:
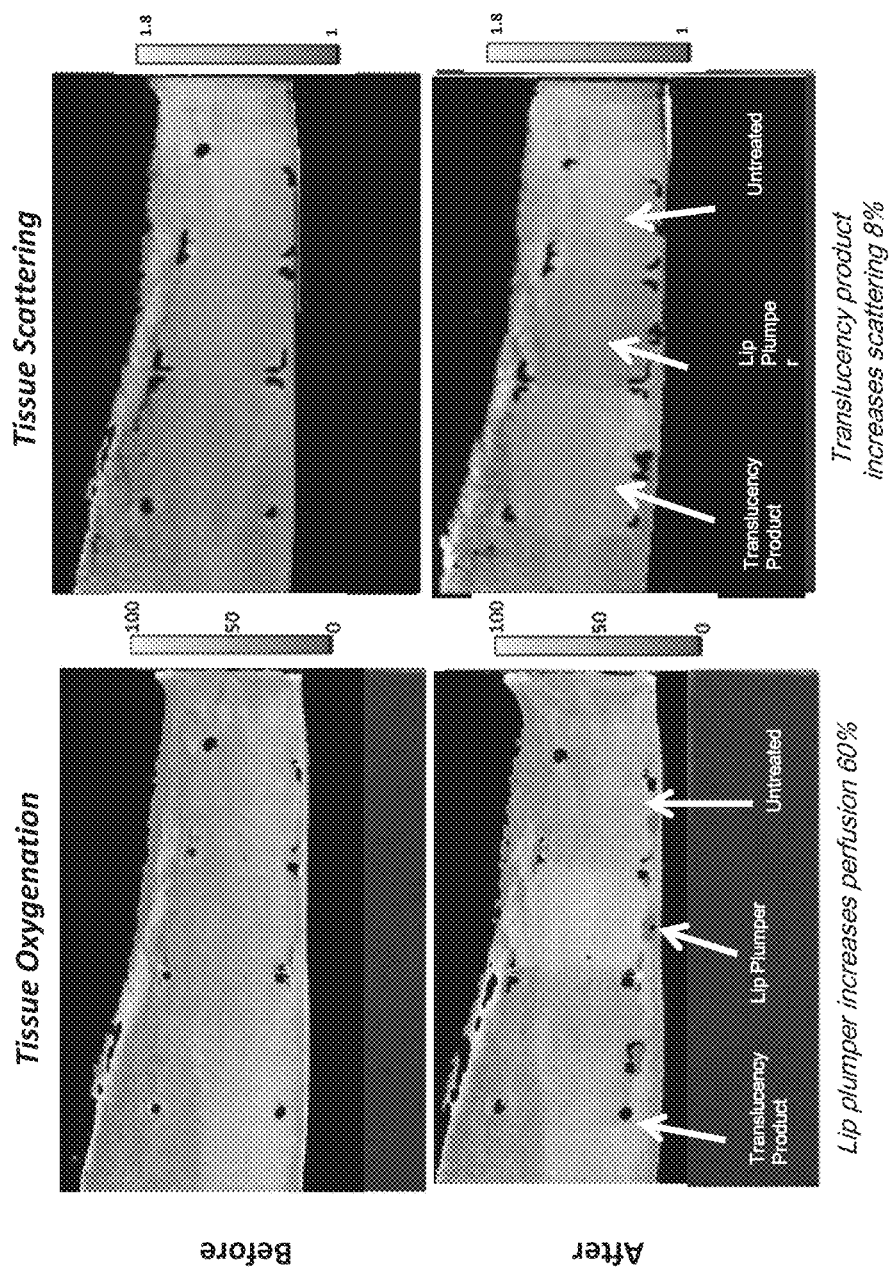
FIG. 23 illustrates imaging of effects of superficial topical products according to embodiments of the present disclosure.
Figure 24:
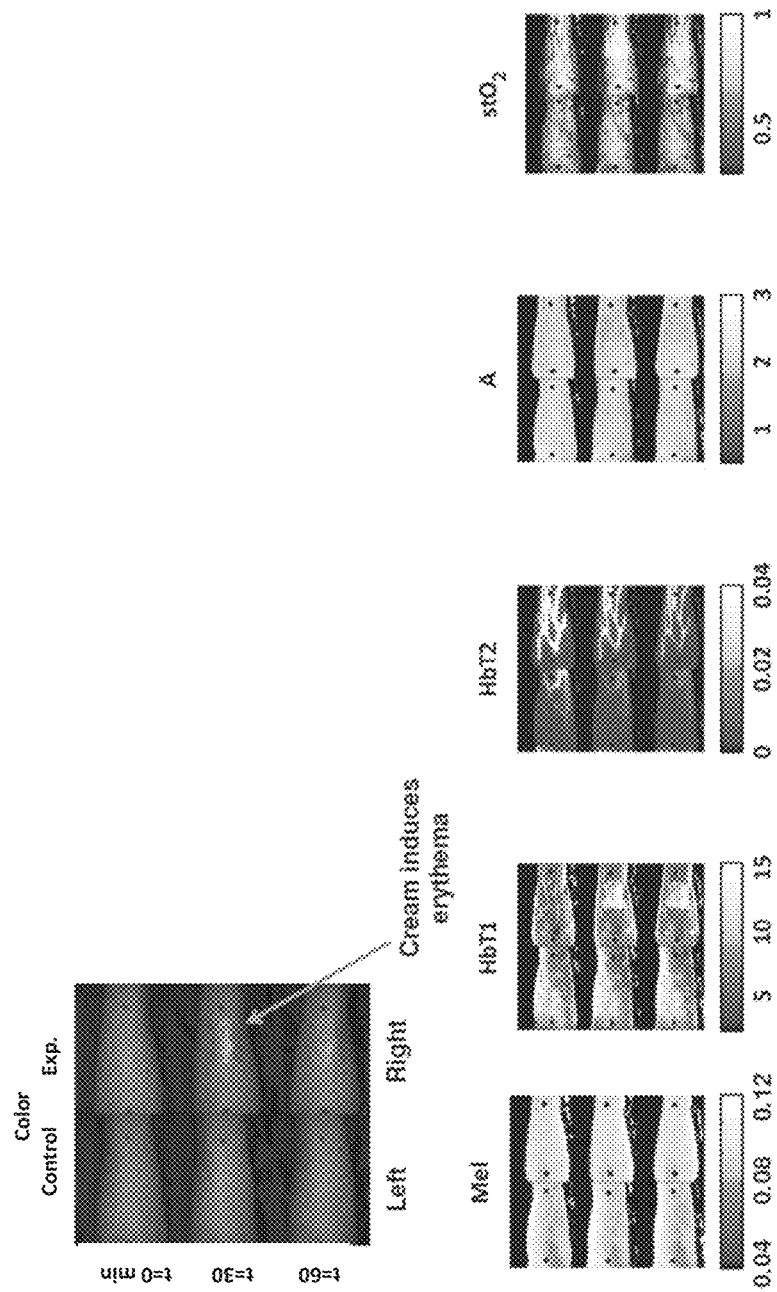
FIG. 24 illustrates imaging of effects of superficial topical products according to embodiments of the present disclosure.
Figure 25:
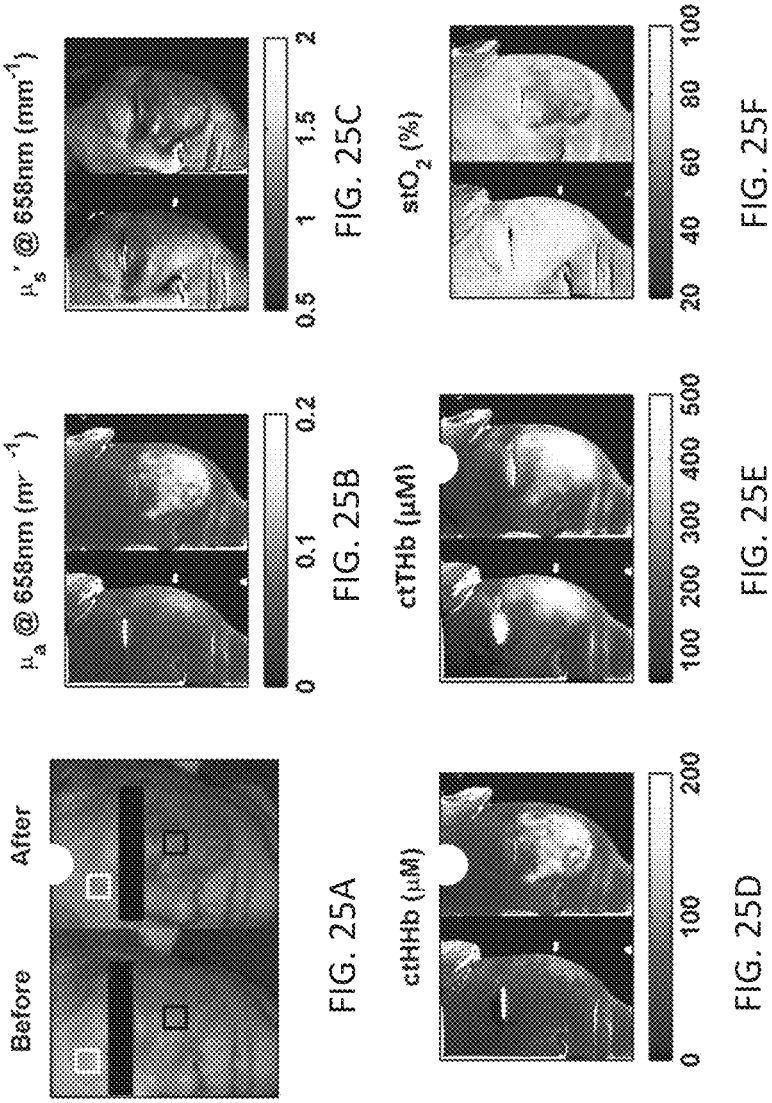
FIGS. 25A, 25B, 25C, 25D, 25E and 25F illustrate imaging effects of deep vascular changes and modifications from laser therapy according to embodiments of the present disclosure.

FIGS. 23 and 24 illustrate imaging of effects of superficial topical products according to embodiments of the present disclosure. The unique, depth-dependent signatures resulting from the present system inform on small- and large-vessel disease by reporting superficial (roughly millimeter or sub-millimeter depths) and deep-tissue (roughly 1 mm or deeper) hemoglobin concentration (i.e. blood volume) measures, respectively. FIGS. 23 and 24 show the effects of a topical "lip plumper" agent designed to create an inflammatory response in the superficial skin (i.e. papillary dermis). FIG. 24 shows that changes/alterations in the superficial contrast from the induced blood perfusion can be isolated from the deeper structures (i.e. veins) which do not show the induced contrast.

FIGS. 25A, 25B, 25C, 25D, 25E and 25F illustrate imaging effects of deep vascular changes and modifications from laser therapy according to embodiments of the present disclosure. FIGS. 25A, 25B, 25C, 25D, 25E and 25F show the effects of pulsed laser therapy, which acutely after treatment creates a large pooling of blood in the deeper skin structures (reticular dermis and sub-cutis).

Figure 26:
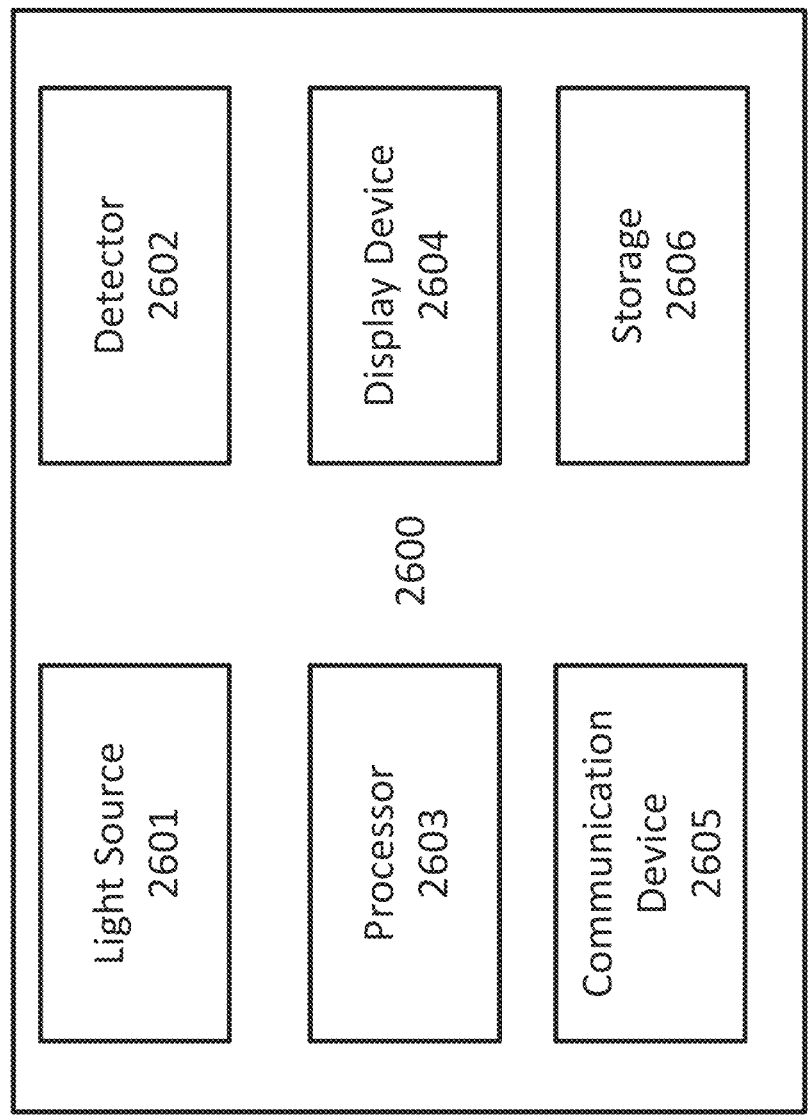
FIG. 26 illustrates an exemplary optical measurement system for use with embodiments of the present disclosure.

FIG. 26 illustrates an exemplary optical measurement system for use with embodiments of the present disclosure. An exemplary optical measurement system 2600 includes a light source 2601 with one or more wavelengths. The light source 2601 is configured to illuminate an area of tissue. The system 2600 includes a detector 2602 configured to capture the light reflecting from the tissue at the one or more illumination wavelengths. The system 2600 includes a processor 2603 configured to compute, based on the detected signal, one or more estimates of tissue vascular health. The system 2600 further includes a display device 2604 configured to display the tissue vascular reactivity or other data. The system 2600 further includes a communication device 2605 (e.g. electronic data transfer) configured to report the tissue vascular reactivity or other data. The system 2600 further includes storage 2606 configured to store the tissue vascular reactivity or other data.

Processor 2603 is configured to separately characterize multiple tissue compartments or regions, based on spatially distinct areas identified in the processed image data. These spatially distinct areas can be lateral changes, such as identifying and/or quantifying regions of high or low perfusion within the image plane, or they can be depth-dependent changes, such as the ability to resolve and quantify pigmentation (~100 μm depths), superficial capillaries (100 μm-1500 μm depths) and deeper blood signatures (1500 μm and deeper), or the ability to quantify the thickness of a callus layer (absorption contrast). Discussions regarding such capabilities are provided above with regard to FIGS. 9, 10A and 10B, where a 3-layer tissue geometry is used to represent and analyze the observed reflectance data using spatial frequency and wavelength contrast. The resulting metrics (absorption, scattering, chromophore concentration, etc.) can then be used individually or in combination, such as, e.g., an index, as described above in regards to FIGS. 6A, 6B, 14A, 14B and 20, to provide estimates of tissue health and/or vascular reactivity.

Processor 2603 is configured to execute instructions stored in storage 2606, where execution of the instructions by the processor 2603 causes the system 2600 to compute various estimates and other data and analyses described herein. Storage 2606 can be any computer readable medium, including non-transitory computer readable medium.

The system 2600 reports an estimate of tissue vascular health, which may include one or more estimates of tissue health and/or risk of tissue injury, based on the concentration, lateral distribution, and/or depth distribution of one or more subsurface tissue constituents exhibiting optical absorption and/or scattering contrast (e.g. blood concentration, blood oxygenation, water/hydration, collagen, lipids, exogenous agents), and/or based on an estimate of vasomotor regulation or vascular reactivity derived from the one or more tissue constituents exhibiting absorption and/or scattering contrast.

The detector 2602 can be configured to provide a single time point capture. The detector 2602 can be a 2D imaging detector array. The 2D imaging detector array may comprise a CCD/CMOS camera. The detector 2602 can be a single-element detector. The single-element detector can be one of a photodiode and an optical fiber relay to a detection system. The detector 2602 can include multiple single-element detectors configured to collect reflected light from multiple tissue locations.

The source 2601 can be configured to create at least one spatially-structure light pattern over the tissue surface. The spatially-structured light is configured to perform spatial frequency domain imaging.

The display 2604 can be one of an interactive touchscreen device, a tablet, and a digital phone. The optical measurement system 2600 can be configured to interface with a computer system, tablet, or digital phone with a wired or wireless connection.

FIG. 27A illustrates an exemplary method for estimating tissue vascular health according to embodiments of the present disclosure. An area of a tissue sample is illuminated 2701, light reflecting from the illuminated area is captured 2702. The light can be captured by a detector configured to capture light reflecting from the tissue at one or more illumination wavelengths. The tissue vascular health or vascular reactivity is assessed and/or estimated 2703 based on the detected or captured light signals, and then displayed and/or otherwise reported 2704.

The estimate of tissue vascular health may include one or more estimates of tissue health and/or risk of tissue injury, based on the concentration, lateral distribution, and/or depth distribution of one or more subsurface tissue constituents exhibiting optical absorption and/or scattering contrast (e.g., blood concentration, blood oxygenation, water/hydration, collagen, lipids, exogenous agents), and/or based on an estimate of vasomotor regulation or vascular reactivity derived from the one or more tissue constituents exhibiting absorption and/or scattering contrast.

As shown in FIG. 27B, a diagnosis of tissue health and/or risk may be generated 2705 from the estimated tissue vascular reactivity of the illuminated area of tissue. This diagnosis may be made either by the practicing clinician or the device itself. A therapy, treatment, treatment product, or a behavioral change may be recommended 2706 in response to the diagnosis. Again, this recommendation may be made either by the practicing clinician or the device itself.

Illuminating the tissue sample 2701 can include illuminating the tissue sample with a spatially-structured light pattern over the tissue surface. The spatially-structured light pattern can be configured to perform spatial frequency domain imaging.

The tissue vascular reactivity of the tissue sample can be assessed 2703 in two ways. In one way, dynamic changes can be measured to probe reactivity directly, such as during a vascular cuff occlusion. In another way, single time point measures are generated, such as blood pooling and capillary perfusion indices, which individually or in combination can be used as an analog/correlate to vascular reactivity. In this way, a method for a simpler and faster clinical examination of vascular health is provided.

In an example of the workflow of the exemplary method shown in FIGS. 27A and 27B, an SFDI dataset would be acquired via illumination (at 2701) and detection (at 2702) of structured and non-structured illumination using both visible and near-infrared wavelengths. The analysis may proceed as depicted in and discussed with regard to FIGS. 4A, 4B, 4C and 4D, where some of the wavelengths have structured illumination, and then this process is repeated at one or more wavelengths to compute chromophore information from the absorption coefficient (blood in a specific layer, $StO_2$, $H_2O$, and/or etc.). In one particular embodiment, the processor (at 2603) may instead compute chromophores directly based on the multi-spectral dataset. Such chromophore information is depicted in and discussed with regards to FIG. 5A, 5B, 6A, 6B or 13. Based on these data, one or more assessments of vascular health may be computed (at 2703). A specific example is described with regards to FIGS. 14A and 14B, where an ulcer risk index is derived from a ratio of superficial and deep hemoglobin signatures. Based on this information, a display and/or report of this information is provided (at 2704), such as is depicted in and described with regards to FIGS. 14A and 14B. This information can then be used to inform a diagnosis (at 2705), such as an assessment that the patient has poor vascular health (e.g. high risk of ulceration). This diagnosis may be made either by the practicing clinician or the device itself. Subsequently, a therapy recommendation may be made (at 2706), such as a more frequent patient monitoring protocol, a recommendation for offloading or footwear, a referral to a specialist, or a recommendation for a medical procedure such as arterial stenting. Again, this recommendation may be made either by the practicing clinician or the device itself.

Figure 28A:
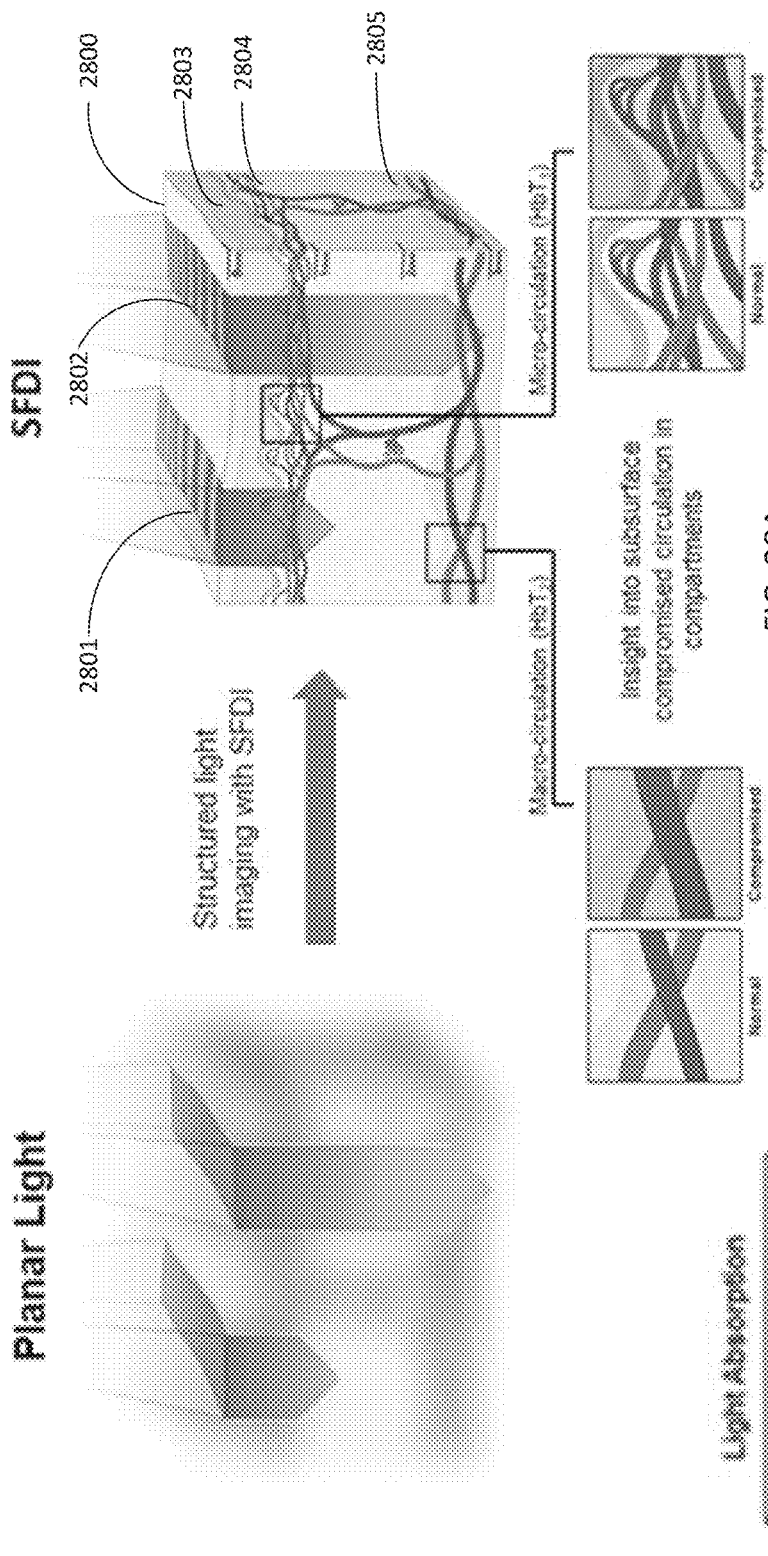
FIG. 28A illustrates a visible and near infrared light propagation in skin. A light transport SFDI model (i.e., Monte Carlo or diffusion) is used with embodiments of the present disclosure for extraction of hemoglobin data from multiple layers.

Turning to FIGS. 28A through 34, systems and methods are disclosed that are directed to the assessment of circulatory complications due to advancement of diabetes are discussed. As shown in FIG. 28A, multi-layer visible and near infrared light propagation models for Spatial Frequency Domain Imaging (SFDI) allow insight into layered perfusion parameters of tissue in skin via extraction of hemoglobin data from the multiple layers of tissue. In embodiments described above, the SFDI algorithm workflow generates two dimensional maps of tissue absorption and scattering which in turn can be used to generate depth-averaged values of chromophores ($HbO_2$, HbR). As shown in FIGS. 28A and 28B, the propagation of light in a wavelength range of $\lambda=400\text{-}1000$ nm is modeled through the layered structure of tissue 2800, which is modeled with average expected distribution of capillaries, arterioles/venules, and melanin. This includes weighting the surface (~top 1 mm) with smaller capillaries and the deeper plexus with larger vasculature. More particularly, the most superficial layer is weighted by capillaries where oxygen diffusion occurs, in skin this approximates the papillary dermis. The deeper layer is weighted more by supplying arterioles and draining venules and is weighted less by capillary density.

Figure 28B:
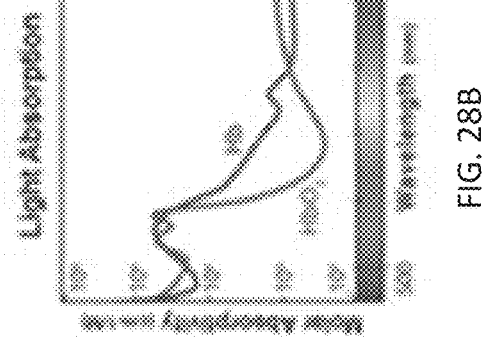
FIG. 28B illustrates a light absorption graph showing sensitivity of visible and near infrared light to hemoglobin.

The transport of multi-spectral light for patterned illumination at many wavelengths is modeled using a forward multi-layer scaled Monte Carlo Model. The Monte Carlo model is built to be a comprehensive representation of light transport in the multiple layers of tissue with adjustable parameters for layer specific optical parameters, including but not limited to absorption, scattering, anisotropy, index of refraction, and vessel packing fraction. The benefit of adding structured (or patterned) light to a typical multi-spectral acquisition is that from a measurement perspective the ill-posed inverse problem can be constrained on an axis beyond wavelengths. This enables fitting for unique solutions that are not possible with multi-spectral illumination. For example, the depth sensitivity can be tuned at multiple wavelengths by changing the frequency of patterned light at all wavelengths to highlight contrast in layers and also measure the tissue scattering. The differential depth sensitivity of patterned light has been described for tomographic measurements before. However, this approach demonstrates a less complicated but more tenable approach for measurement of tissue by outputting depth dependent chromophore information (HbT1, HbT2, and melanin) from measured raw data but anchored by a priori knowledge of tissue architecture. FIGS. 28A and 28B shows an illustration of how this is accomplished for skin. As an example, FIG. 28A shows skin overlaid with the differential depth sensitivity of visible 2801 and near-infrared 2802 light. The skin layers highlight the superficial layer of melanin 2803, a second layer of capillary-weighted microvasculature in the superficial dermis 2804 and larger arterioles/venules in deeper dermis 2805. This method is able to probe all these layers and measure layer specific information. The resulting outputs are: melanin in top layer of skin (~epidermis 2803; ~150 microns deep), capillary weighted HbT1 in top 1-2 mm of the skin (~papillary dermis 2804), and arteriole-venule weighted HbT2 in next 2-4 mm of the skin (~reticular dermis 2805). In this method, layer specific tissue oxygen saturation and scattering is also modeled. However, exemplary embodiments include a measurement of volume averaged mixed arterial-venous measure of tissue oxygen saturation (StO2) and tissue scattering parameter (A) in order to reduce the complexity of the inverse model.

Figure 29B:
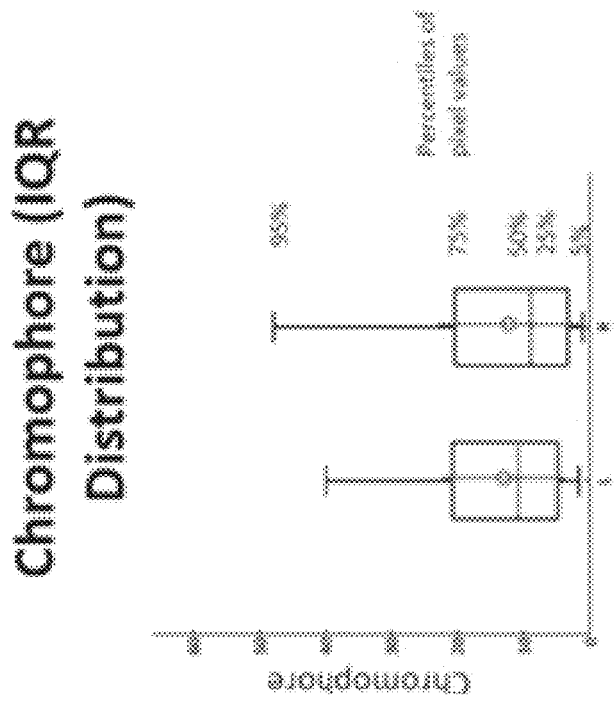
FIG. 29B illustrates a graph showing summarized intensity values (median, IQR and mean) of the extracted chromophore (i.e. hemoglobin) data distributed over the mapped image of an individual one of the chromophores in FIG. 29A.
Figure 29A:
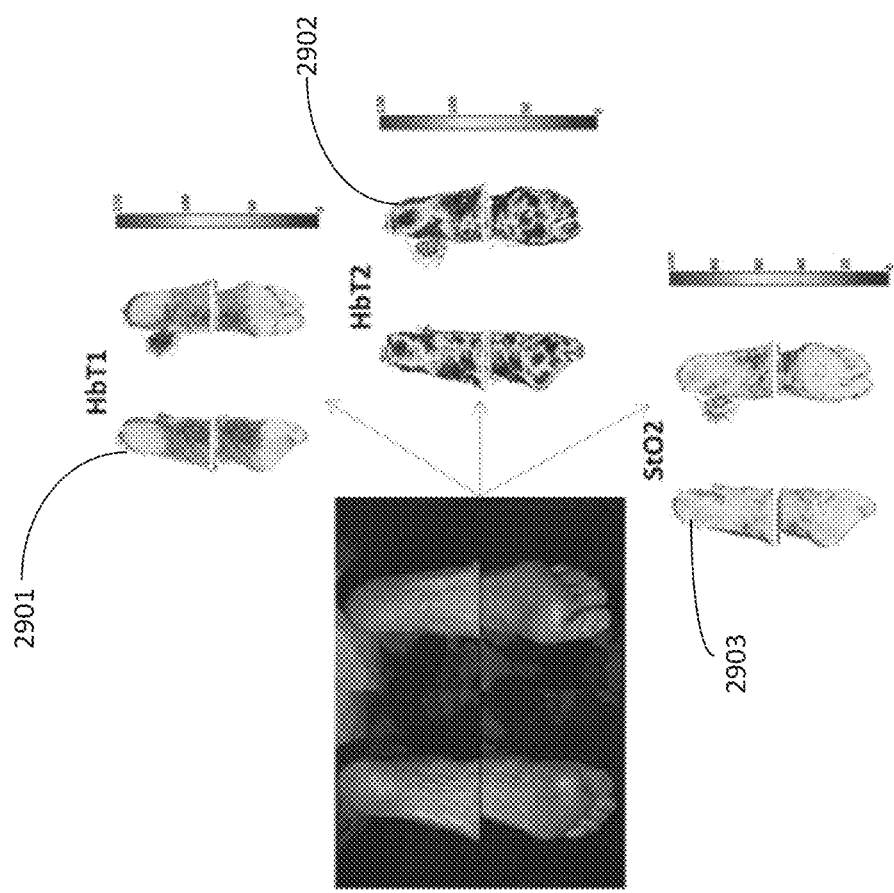
FIG. 29A illustrates a flowchart of multi-layer SFDI imaging of a patient's feet and foot perfusion map showing the intensity values of the multi-layer extracted hemoglobin data.

As described above, the tissue relevant result of this measurement method are foot perfusion maps 2901, 2902 and 2903 of layer specific chromophores over a large area as shown in FIG. 29A. The resulting data can then be analyzed in a number of ways. In the example here, the distribution of pixel values in an entire foot can be characterized by creating a box and whisker plot that show values of the minimum, median, percentile ranges, interquartile ranges, maximum for each chromophore. Alternatively, mean and standard deviation values can be used to represent the foot. Alternatively, region-wise values can be assessed based on specific areas related to known angiosomes (or perfusion zones) of the foot. The goal for this method is to be able to provide a single value that can be used when analyzing large cohort data to get insight on population perfusion characteristics.

A clear benefit of this method is the additional insight into circulation of patients with diabetes. FIGS. 30A, 30B and 30C show foot perfusion map images of representative patients with and without diabetes. The color bar on the left of the images applies to both images and the y-axis represent the distribution of the values shown in the adjacent box and whisker plots for these representative patients. Specifically, referring to FIGS. 30A and 30B, the foot perfusion map images for representative patients with and without diabetes show for patients with diabetes a broad decrease (color map is more dark gray in this scale) in capillary-weighted HbT1 measurement and a broad increase in StO2 (color map is more dark gray in the represented scale) compared to patients with no diabetes. For these patients, a 38% decrease in median HbT1 values and 25% increase in median StO2 value was measured from patients with no diabetes to patients with diabetes. These physiological measurements are consistent with clinical observation in patients with diabetes.

Others have observed clinically that patients with diabetes often times have bounding pulses and hyper-perfusion. Invasive measurements of blood oxygenation have shown in small cohorts that arterio-venous shunting occurs in patients with sensory neuropathy. Experts have hypothesized that with the onset of sensory neuropathy that occurs with diabetes progression, patients lose sympathetic tone and vasomotor regulation. This results in a short-circuit of capillaries in the most distal vasculature in the foot. Hemoglobin is shunted from the capillaries via the thoroughfare due to poor regulation and the result is hyperperfusion and poor oxygen extraction. These are the conditions ripe for onset of a neuro-ischemic ulcer. To this date, there has been no non-invasive manner to measure this circulation compromise.

Figure 31B:
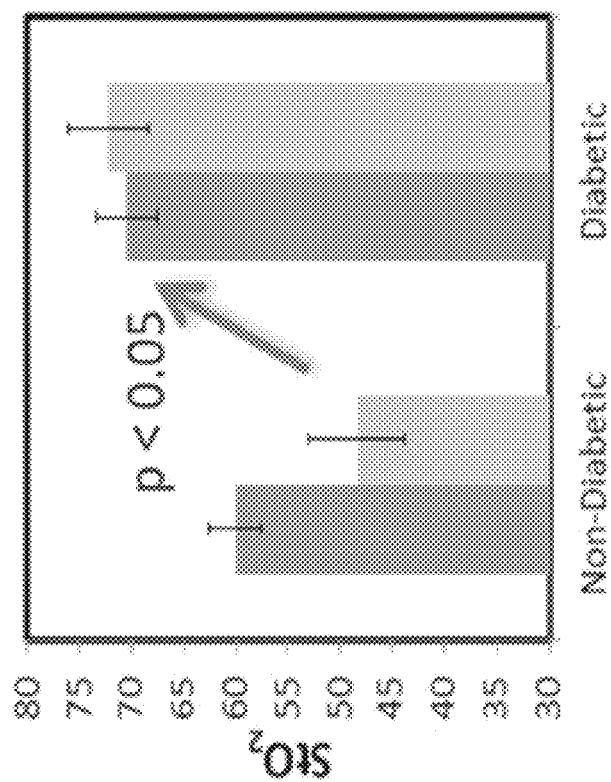
FIG. 31B illustrates a graph comparing the median StO2 for non-diabetic patients with and without PVD, and the median HbT1 for diabetic patients with and without PVD.
Figure 31A:
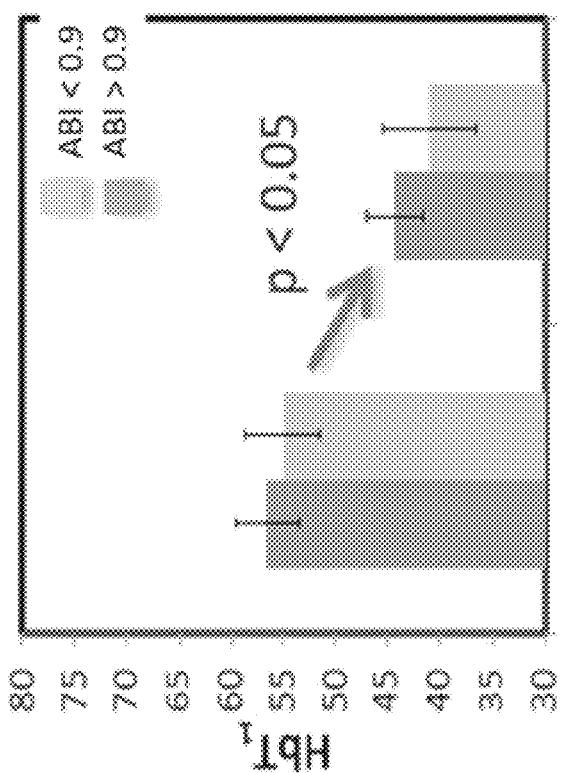
FIG. 31A illustrates a graph comparing the median HbT1 for non-diabetic patients with and without PVD and the median HbT1 for diabetic patients with and without PVD.

Clinically, protective sensation loss is used as a correlation to circulatory compromise in patients with diabetes. According to exemplary embodiments of the present disclosure, the hemoglobin being shunted away from the capillaries can be measured by measuring the HbT1 and the corresponding degradation in oxygen extraction due to elevated StO2. The combination of these factors is a direct measurement of inadequate capillary perfusion coupled with poor oxygen extraction; a hallmark for a patient with diabetes at risk for non-healing ulcer. For an objective comparison over a larger group, the median values of HbT1 and StO2 was measured for a number of feet to do a comparison for patients with and without diabetes. In this cohort, FIGS. 31A and 31B show a significantly lower median value of HbT1 and significantly higher StO2 in patients with diabetes than in patients with no diabetes. This data was analyzed for patients with and without diagnosed vascular disease. The result is that there is a significant ($p<0.05$) decrease in HbT1 and increase in StO2 for patients with diabetes regardless of the status of peripheral disease. Specifically, cohort data shows that limbs of patients with diabetes and no PVD have significantly lower median HbT1 (n=24, HbT1 mean=56.6±3.0) than those patients without diabetes and PVD (n=26, mean HbT1 mean=44.3±2.7). For this same group, a higher StO2 (StO2 mean=70.6±2.9 vs mean=60.0±2.5) was measured regardless of status of vascular disease. This represents a 22% decrease in HbT1 and 18% increase in StO2 for the median values in these groups. The p-value ($p<0.05$) shows statistical significance in these parameters between the all non-diabetics and diabetics using a t-test.

Another benefit of these direct measurements of circulation is earlier detection of disease progression. Conventionally, the first clinical data point used for ulcer stratification is onset of protective sensation loss or neuropathy. This happens over time as circulation is compromised to the peripheral nerves and the peripheral nerves are damaged. According to exemplary embodiments of the present disclosure, systems and methods are provided that enable a direct measure of circulation prior to the sensation loss providing an opportunity for patient management/intervention. An example analysis of patients with diabetes in two groups is presented in FIGS. 32A and 32B. First, a patient population with no sensation loss is presented in two groups: diabetes diagnosis for less than 10 years and greater than 10 years. The group with diabetes for greater than 10 years show a relative decrease in HbT1 and increase in StO2; an observation that is consistent with what was described above. Furthermore, these values for asymptomatic subjects (diabetes>10 years) match what is seen with patients with known sensation loss (regardless of time since diabetes diagnosis). Comparing the mean of the median foot map values shows that patients with diabetes and sensory neuropathy (sensory loss) have significantly lower HbT1 (~17% lower) and higher StO2 (~17% higher) compared to patients with diabetes for less than 10 years. Furthermore, patients with diabetes for longer than 10 years and no sensory loss show a similar circulation profile to those patients with sensory neuropathy. The cumulative data supports the observation that circulation loss precedes sensory loss and the method presented herein could provide an early insight into the progressive damage that occurs due to lack of circulation. This information is critical for identifying the foot that is truly at risk for non-healing ulcers due to diabetes severity.

Figure 33B:
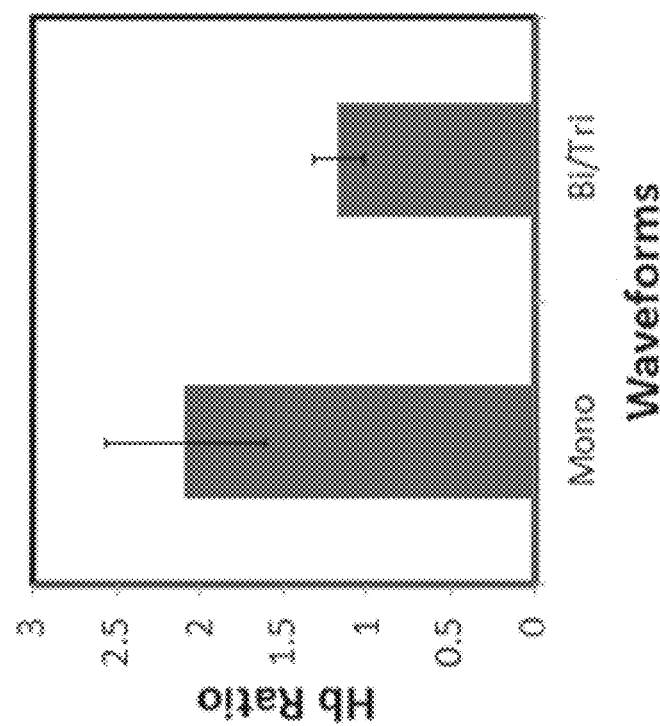
FIG. 33B illustrates a graph comparing the ratio of the median HbT2 and HbT1 values for patients with PVD (monophasic waveforms) and without PVD (biphasic/triphasic waveforms).
Figure 33A:
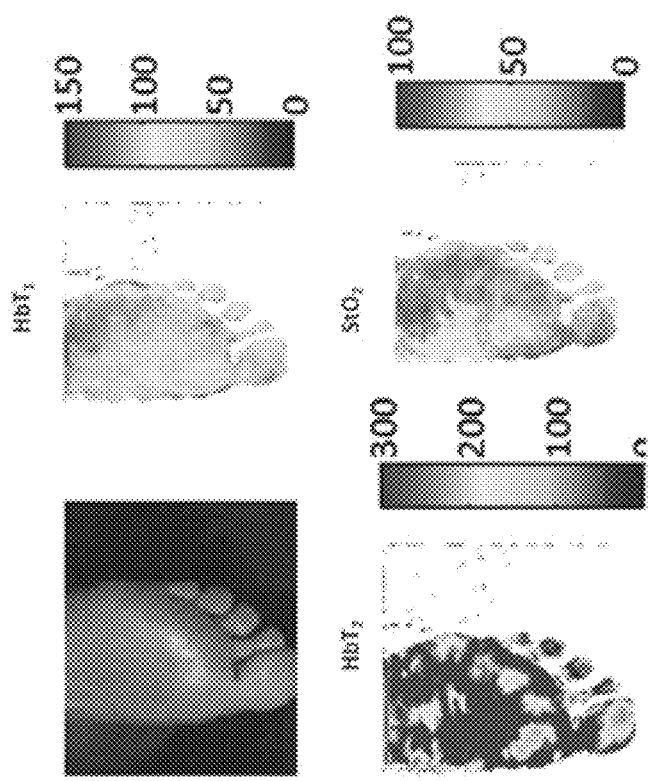
FIG. 33A illustrates a flowchart of multi-layer SFDI imaging of a patient's feet and foot perfusion map showing the intensity values of chromophores corresponding to multi-layer extracted hemoglobin data.

Another benefit of layered measurements is that such measurements enable the compartment distribution in patients with diabetes to be analyzed. The discussions above highlighted the decrease in HbT1 that occurs as diabetes progresses and nerves are damaged. The result is ineffective microcirculation due to arterio-venous shunting. However, many patients with diabetes suffer from upstream issues in peripheral perfusion. Larger tibial vessels in the lower limb and even larger supplying arteries (i.e. popliteal, femoral, etc.) can become compromised as peripheral vascular disease (PVD) occurs in this population. As mentioned above, diagnosis of PVD is notoriously hard in patients with diabetes due to the poor performance of current non-invasive tests (ABIs, TBIs, waveforms). This is mainly due to the non-compressible nature of the vessels often observed in this patient population. However, as depicted in FIGS. 33A and 33B, taking a ratio of the median HbT2 to the median HbT1 gives insight into peripheral vascular disease in patients. As depicted, a significant increase in HbT2 relative to HbT1 was measured for patients with diabetes and known PVD as determined by an expert listening to waveforms. For the purposes of this study, monophasic waveforms measured by Doppler are being used here to represent patients with peripheral vascular disease. Biphasic/triphasic waveforms are considered patients without PVD. In this example, we observe that the Hb ratio for median HbT2 and HbT1 values are greater for subjects (2.1±0.5 vs. 1.2±0.1) with monophasic waveforms. This represents a 57% increase in the Hb ratio for patients considered to have PVD. This is likely due to pooling that can occur due to inadequate blood supply and drainage as upstream arteries become blocked. The data shown in FIG. 33B demonstrates a higher sensitivity to PVD in patients with PVD than conventional method (in particular when compared to current standard of ABI) and highlights the utility of this method to identify patients at the highest risk for ulceration prior to developing the primary ulcer.

Figure 34:
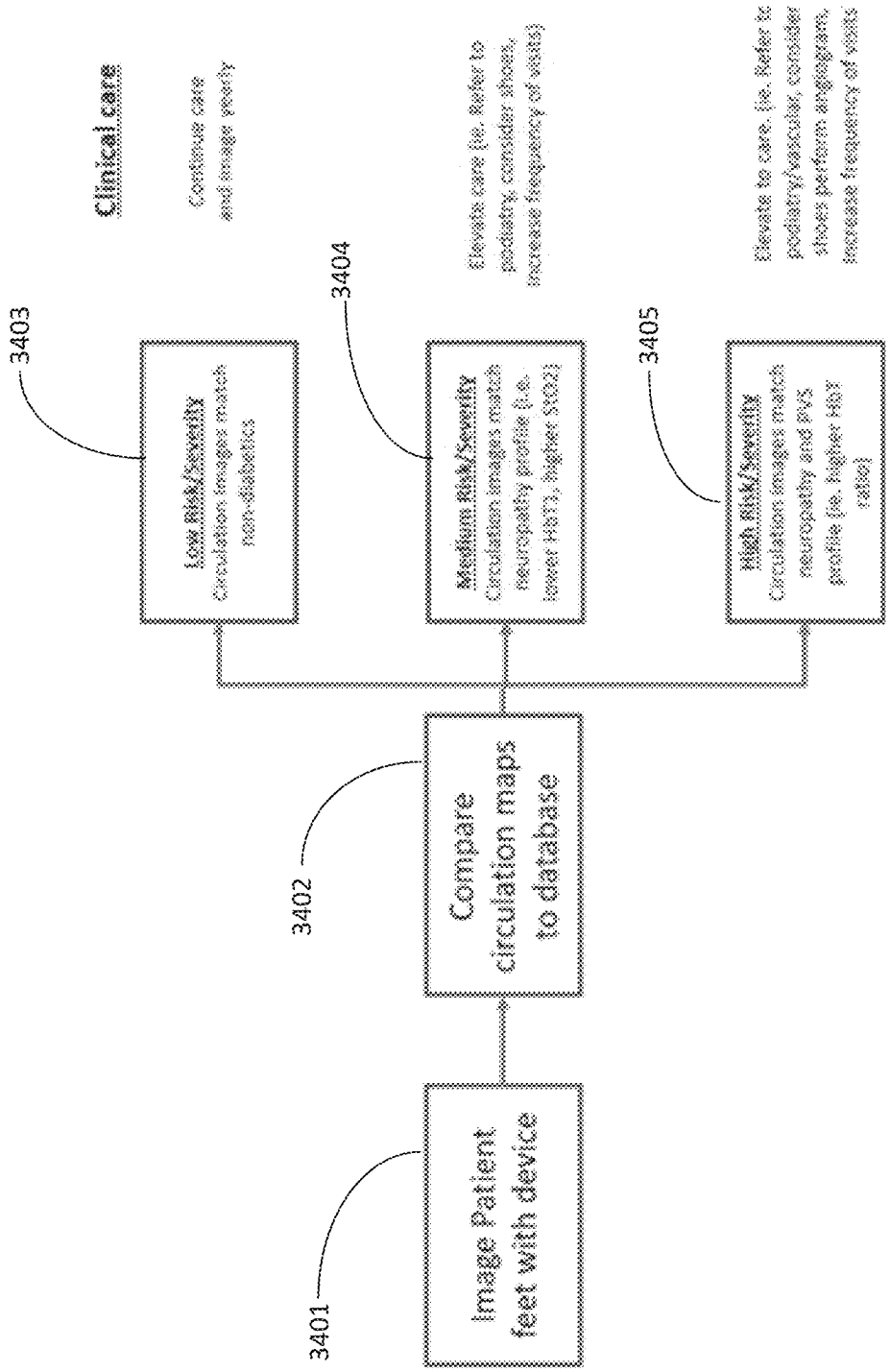
FIG. 34 illustrate a flowchart of a workflow for using apparatus and method for stratifying diabetic risk based on severity.

According to exemplary embodiments of the present disclosure, a rapid and quantitative workflow is provided to identify patients in all settings (but most importantly primary care/community) that require elevated care (i.e. referral to podiatry/vascular, better shoes, more frequency check-ups) so preventive action can be taken in a more targeted fashion for the highest risk patients. A typical workflow for stratifying diabetic risk based on severity is shown in FIG. 34. The patient's feet are first imaged 3401 and then circulation maps and representative values (i.e. median, mean, IQR) generated from the extracted layer data can be compared 3402 to database maps or values to characterize 3403, 3404 and 3405 severity/risk of the patient and manage preventive care.

The systems and methods presented herein can be used to develop foot perfusion or Hb and StO profiles of non-diabetic patients, and thus a look up table or database of typical values or image maps generated from the same that can be used as a standard against which to compare data from a patient's imaged feet.

In the study discussed with regard to FIGS. 30A, 30B, 30C, 31A and 31B, it was found that the average median foot HbT1 values for non-diabetic patients (n=26) was 56.6 with a standard error of 3.0. The StO2 values for this same group were 60.0% with a standard error of 2.5%. It was found that the average median foot values for diabetic patients (n=26) was 44.3 with a standard error of 2.7. The StO2 values for this same group were 70.6% with a standard error of 2.9%. The representative values in this suggest that a reduction of 22% in HbT1 and increase of 18% would be an indication of circulation loss due to diabetes.

Figures 32A, 32B:
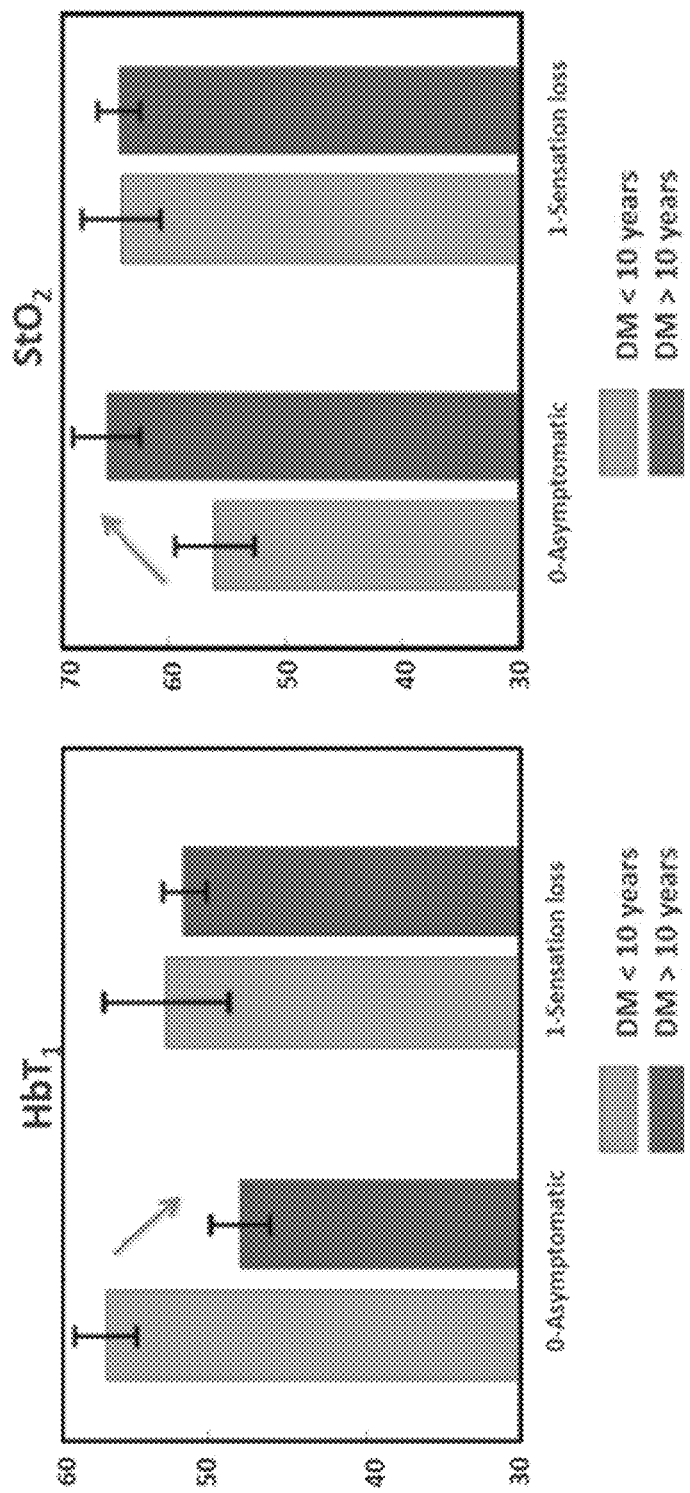
FIG. 32A illustrates a graph comparing the mean of the median foot map values of HbT1 for patients with and without sensory neuropathy and being diabetic for greater than and less than 10 years.
FIG. 32B illustrates a graph comparing the mean of the median foot map values of StO2 for patients with and without sensory neuropathy and being diabetic for greater than and less than 10 years.

In the study discussed with regard to FIGS. 32A and 32B, patients with diabetes and sensory neuropathy (sensory loss) have significantly lower HbT1 (~17% lower) and higher StO2 (~17% higher) compared to patients with diabetes and no sensation loss, for patients with diabetes for less than 10 years. This study shows that such changes in baseline changes could be indicators of sensory loss. Furthermore, these circulation changes could precede sensation loss as evidenced by the similarity in circulation profile (>17% decrease in HbT1 and >17% increase in StO) for patients with diabetes for greater than 10 years and those with sensation loss.

In the study discussed with regard to FIGS. 33A and 33B, it was found that the average median foot Hb ratio (HbT2/HbT1) values are greater for subjects (2.1±0.5 vs. 1.2±0.1) with monophasic waveforms. This represents a 57% increase in the Hb ratio for patients considered to have PVD.

The studies discussed above were used to describe ranges of representative values in patient population.

According to one embodiment of the present disclosure, an optical measurement device includes a light source with one or more wavelengths, the light source is configured to illuminate an area of tissue; a detector configured to capture the light reflecting from one or more layers of the tissue at the one or more illumination wavelengths; a processor configured to compute, based on the detected signal of layer extracted circulatory data, one or more estimates of tissue vascular health, and a display or communication device (e.g., electronic data transfer) configured to store or report the tissue vascular health.

According to one embodiment of the present disclosure, the detected signal of layer extracted circulatory data comprising data reflecting a distribution of hemoglobin ("Hb") in different layers of skin.

According to one embodiment of the present disclosure, the extracted circulatory data is extracted using a combination of structured light in the visible and near-infrared regime.

According to one embodiment of the present disclosure, the extracted circulatory data is extracted Hb data extracted from two layers of skin—a first layer referred to as the superficial papillary dermis (capillary-weighted) and a second layer referred to as the deeper reticular dermis (arteriole/venule weighted).

According to one embodiment of the present disclosure, the extracted showing a change in circulatory data that correlates with and/or precedes protective sensation loss.

According to one embodiment of the present disclosure, the extracted showing a change in circulatory data that correlates poor O2 extraction as a result of compromised transport and/or low consumption rather than excessive blood supply.

According to one embodiment of the present disclosure, the extracted showing a change in compartment distribution that correlates to the status of peripheral vascular disease ("PVD).

According to one embodiment of the present disclosure, an optical measurement apparatus to measure circulation in the limbs of patients with diabetes that correlates to severity of the progressive damage due to diabetes.

According to one embodiment of the present disclosure, the optical measurement apparatus uses visible and near-infrared light.

According to one embodiment of the present disclosure, the optical measurement apparatus uses structured light.

According to one embodiment of the present disclosure, the optical measurement apparatus uses a CCD or CMOS detection array to capture images of the remitted light.

According to one embodiment of the present disclosure, the optical measurement apparatus displays images of the processed chromophore data.

According to one embodiment of the present disclosure, the optical measurement apparatus displays images of the processed data and allows selection of values.

According to one embodiment of the present disclosure, the optical measurement apparatus displays images and statistical distribution of values.

According to one embodiment of the present disclosure, a method that measures parameters that describes metrics of circulation loss due to progression of diabetes.

According to one embodiment of the present disclosure, the method measures changes in layer-specific Hb.

According to one embodiment of the present disclosure, the method measures lack of oxygen extraction due to capillary dysfunction.

According to one embodiment of the present disclosure, the method identifies circulation loss for patients with neuropathy.

According to one embodiment of the present disclosure, the method identifies circulation loss prior to loss in protective sensation.

According to one embodiment of the present disclosure, the method measures parameters that describes circulation loss due to peripheral vascular disease in patients with diabetes.

According to one embodiment of the present disclosure, the method measures changes in layer-specific Hb.

According to one embodiment of the present disclosure, the method measures increase in HbT2.

According to one embodiment of the present disclosure, a method that enables the generation of maps of lower limb perfusion for extraction of regional values of foot specific perfusion.

According to one embodiment of the present disclosure, an optical measurement system comprises a light source with one or more wavelengths, configured to illuminate an area of tissue. The optical measurement system further comprises a detector configured to capture the light reflecting from the tissue at the one or more illumination wavelengths, a processor configured to compute, based on the detected signal, one or more estimates of tissue vascular health, and a display or communication device (e.g. electronic data transfer) configured to store or report the tissue vascular reactivity.

According to a further embodiment of the present disclosure, the estimate of tissue vascular health may include one or more estimates of tissue health and/or risk of tissue injury, based on the concentration, lateral distribution, and/or depth distribution of one or more subsurface tissue constituents exhibiting optical absorption and/or scattering contrast (e.g. blood concentration, blood oxygenation, water/hydration, collagen, lipids, exogenous agents), and/or based on an estimate of vasomotor regulation or vascular reactivity derived from the one or more tissue constituents exhibiting absorption and/or scattering contrast.

According to a further embodiment of the present disclosure, the detector is configured to provide a single time point capture.

According to a further embodiment of the present disclosure, the detector is a 2D imaging detector array.

According to a further embodiment of the present disclosure, the 2D imaging detector array comprises a CCD/CMOS camera.

According to a further embodiment of the present disclosure, the detector is a single-element detector.

According to a further embodiment of the present disclosure, the single-element detector is one of a photodiode and an optical fiber relay to a detection system.

According to a further embodiment of the present disclosure, the detector includes multiple single-element detectors configured to collect reflected light from multiple tissue locations.

According to a further embodiment of the present disclosure, the source is configured to create at least one spatially-structure light pattern over the tissue surface.

According to a further embodiment of the present disclosure, the spatially-structured light is configured to perform spatial frequency domain imaging.

According to a further embodiment of the present disclosure, the display is one of an interactive touchscreen device, a tablet, and a digital phone.

According to a further embodiment of the present disclosure, the optical measurement device is configured to interface with a computer system, tablet, or digital phone with a wired or wireless connection.

According to an embodiment of the present disclosure, a method to estimate tissue vascular health of a tissue sample comprises illuminating the tissue sample; and assessing tissue vascular reactivity of the tissue sample at a single time point capture.

According to an embodiment of the present disclosure, a method to estimate tissue vascular health of a tissue sample comprises illuminating an area of the tissue sample, capturing light reflecting from the illuminated area of tissue by a detector configured to capture light reflecting from the tissue at one or more illumination wavelengths, and estimating tissue vascular health from the detected or captured light signals.

According to a further embodiment of the present disclosure, the estimate of tissue vascular health may include one or more estimates of tissue health and/or risk of tissue injury, based on the concentration, lateral distribution, and/or depth distribution of one or more subsurface tissue constituents exhibiting optical absorption and/or scattering contrast (e.g., blood concentration, blood oxygenation, water/hydration, collagen, lipids, exogenous agents), and/or based on an estimate of vasomotor regulation or vascular reactivity derived from the one or more tissue constituents exhibiting absorption and/or scattering contrast.

According to a further embodiment of the present disclosure, a method further comprises reporting or displaying the estimated tissue vascular health of the illuminated area of tissue.

According to a further embodiment of the present disclosure, a method further comprises generating a diagnosis of tissue health and/or risk from the estimated tissue vascular reactivity of the illuminated area of tissue.

According to a further embodiment of the present disclosure, a method further comprises recommending a therapy, treatment, a treatment product, or a behavioral change in response to the diagnosis.

According to a further embodiment of the present disclosure, illuminating the tissue sample includes illuminating the tissue sample with a spatially-structured light pattern over the tissue surface.

According to a further embodiment of the present disclosure, illuminating the tissue sample includes illuminating the tissue sample with a spatially-structured light pattern over the tissue surface.

According to a further embodiment of the present disclosure, the spatially-structured light pattern is configured to perform spatial frequency domain imaging.

All features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. Express recitation of every possible combination and substitution is overly burdensome, especially given that the permissibility of each and every such combination and substitution will be readily recognized by those of ordinary skill in the art upon reading this description.

In many instances, entities are described herein as being coupled to other entities. It should be understood that the terms "coupled" and "connected" (or any of their forms) are used interchangeably herein and, in both cases, are generic to the direct coupling of two entities (without any non-negligible (e.g., parasitic intervening) entities) and the indirect coupling of two entities (with one or more non-negligible intervening entities). Where entities are shown as being directly coupled together, or described as coupled together without description of any intervening entity, it should be understood that those entities can be indirectly coupled together as well unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. An optical measurement system to extract the levels of hemoglobin and oxygen saturation in different layers of tissues, comprising:
    a light source configured to illuminate an area of tissue of a patient with light signals comprising a plurality of illumination wavelengths and a spatially-structured light pattern;
    a detector configured to coincidentally capture light signals reflecting from a first layer of tissue within the illumined area of tissue and reflecting from a second layer of tissue within the illuminated area of tissue at the plurality of illumination wavelengths;
    a processor configured to compute, within the illuminated area of the tissue from the captured light signals, tissue oxygen saturation levels and layer of tissue specific hemoglobin levels, and estimate the severity of circulatory complications due to diabetes of the illuminated area of tissue as a function of the determined tissue oxygen saturation levels and layer of tissue specific hemoglobin levels in each of the first and second layers of tissue within the illuminated area of tissue of the patient; and
    a display or communication device configured to display or report the estimated severity of circulatory complications within the illuminated area of tissue.

2. The system of claim 1 wherein the light source illuminates the tissue with visible and near-infrared light.

3. The system of claim 1 wherein the detector is one of a 2D imaging detector array and a single-element detector.

4. The system of claim 1 wherein the detector is one of a 2D imaging detector array comprising a CCD/CMOS camera and a single-element detector comprising one of a photodiode and an optical fiber relay to a detection system.

5. The system of claim 1 wherein the display device displays images of the processed data from captured light signals, displays images of the processed data and enables selection of values, or displays images and statistical distribution of values.

6. The system of claim 1 wherein the display device is one of an interactive touchscreen device, a tablet, and a digital phone.

7. The system of claim 1 wherein the optical measurement system is configured to interface with a computer system, tablet, or digital phone with a wired or wireless connection.

8. A method to extract the levels of hemoglobin and oxygen saturation in different layers of tissues of a patient to estimate the level of severity of circulatory complications due to diabetes, comprising:
    illuminating an area of tissue of a patient with light signals comprising a plurality of illumination wavelengths and a spatially-structured light pattern;
    coincidentally capturing light signals reflecting from a first layers of tissue within the illuminated area of tissue and reflecting from a second layer of tissue within the illuminated area of tissue by a detector configured to capture light signals reflecting from the first and second layers of tissue within the illuminated area of tissue at the plurality of illumination wavelengths;
    determining, within the illuminated area of the tissue from the captured light signals, tissue oxygen saturation levels and layer of tissue specific hemoglobin levels,
    estimating the severity of circulatory complications due to diabetes of the illuminated area of tissue as a function of the determined tissue oxygen saturation levels and layer of tissue specific hemoglobin in each of the first and second layers of tissue within the illuminated area of tissue of the patient; and
    reporting or displaying with a display or communication device the estimated severity of circulatory complications within the illuminated area of tissue.

9. The method of claim 8 further comprising generating a diagnosis of tissue health and/or risk from the severity of the progressive damage due to diabetes for the illuminated area of tissue.

10. The method of claim 9 further comprising recommending a therapy, treatment, a treatment product, or a behavioral change in response to the diagnosis.

11. The method of claim 8 wherein the step of illuminating the tissue includes illuminating the tissue with visible and near-infrared light.

12. The method of claim 8 wherein the step of illuminating the tissue includes illuminating the tissue with structured light.

* * * * *